United States Patent [19]

Aquino et al.

[11] Patent Number: 5,739,129
[45] Date of Patent: Apr. 14, 1998

[54] CCK OR GASTRIN MODULATING 5-HETEROCYCLIC-1, 5 BENZODIAZEPINES

[75] Inventors: Christopher Joseph Aquino, Long Beach, Wash.; Elizabeth Ellen Sugg, Durham; Jerzy Ryszard Szewczyk, Chapel Hill, both of N.C.

[73] Assignee: Glaxo Wellcome Inc., RTP, N.C.

[21] Appl. No.: 722,191

[22] PCT Filed: Apr. 12, 1995

[86] PCT No.: PCT/US95/04163

§ 371 Date: Oct. 11, 1996

§ 102(e) Date: Oct. 11, 1996

[87] PCT Pub. No.: WO95/28419

PCT Pub. Date: Oct. 26, 1995

[30] Foreign Application Priority Data

Apr. 14, 1994 [GB] United Kingdom .................. 9407433
Oct. 14, 1994 [GB] United Kingdom .................. 9420783

[51] Int. Cl.⁶ .................................................. A61K 31/55
[52] U.S. Cl. ...................................... 514/221; 540/518
[58] Field of Search ........................... 514/221, 507, 514/518; 540/507, 518

[56] References Cited

U.S. PATENT DOCUMENTS

| | | | |
|---|---|---|---|
| 4,490,364 | 12/1984 | Rivier et al. | 424/177 |
| 4,988,692 | 1/1991 | Gasc et al. | 514/221 |
| 5,187,154 | 2/1993 | Phillips et al. | 514/12 |
| 5,585,376 | 12/1996 | Finch et al. | 514/221 |
| 5,597,915 | 1/1997 | Chambus et al. | 514/221 |
| 5,618,812 | 4/1997 | Pineiro et al. | 514/221 |
| 5,641,775 | 6/1997 | Finich et al. . | |

FOREIGN PATENT DOCUMENTS

| | | |
|---|---|---|
| A0284256 | 9/1988 | European Pat. Off. . |
| A 0376849 | 7/1990 | European Pat. Off. . |
| A 9314074 | 7/1993 | WIPO . |
| A9424149 | 10/1994 | WIPO . |
| 94/25445 | 11/1994 | WIPO . |
| 95/03284 | 2/1995 | WIPO . |
| 95/03285 | 2/1995 | WIPO . |
| 95/28391 | 10/1995 | WIPO . |

*Primary Examiner*—James H. Reamer
*Attorney, Agent, or Firm*—Robert H. Brink

[57] ABSTRACT

Compounds of general formula (I) and physiologically salts thereof, processes for their preparation and their use as modulators of the effects of gastrin and CCK.

17 Claims, No Drawings

CCK OR GASTRIN MODULATING 5-HETEROCYCLIC-1, 5 BENZODIAZEPINES

This invention relates to 5-heterocyclo-1,5-benzodiazepine derivatives, to processes for their preparation, to pharmaceutical compositions containing them and to their use in medicine. More particulary, it relates to compounds which exhibit agonist activity for CCK-A receptors thereby enabling them to modulate the hormones gastrin and cholecystokinin (CCK) in mammals.

Cholecystokinins (CCK) and gastrin are structurally related peptides which exist in gastrointestinal tissue and in the central nervous system. Cholecystokinins include CCK-33, a neuropeptide of thirty-three amino acids in its originally isolated form, its carboxyl terminal octapeptide, CCK-8 (also a naturally occurring neuropeptide), and 39- and 12-amino acid forms. Gastrin occurs in 34-, 17- and 14-amino acid forms, with the minimum active sequence being the C-terminal tetrapeptide, Trp-Met-Asp-Phe-$NH_2$ (CCK-4) which is the common structural element shared by both CCK and gastrin.

CCK and gastrin are gastrointestinal hormones and neurotransmitters in the neural and peripheral systems and perform their respective biological roles by binding to particular receptors located at various sites throughout the body. There are at least two subtypes of cholecystokinin receptors termed CCK-A and CCK-B and both are found in the periphery and in the central nervous system.

The CCK-A receptor, commonly referred to as the "peripheral-type" receptor, is primarily found in the pancreas, gallbladder, lieure, pyloric sphincter and on vagal afferent nerve fibers. Type-A CCK receptors are also found in the brain in discrete regions and serve to provide a number of CNS effects. Due to the ability of CCK-8 and Type-A CCK-selective agonists to suppress food intake in several animal species, considerable interest has been generated toward the development of new substances which function as Type-A receptor-selective CCK agonists in order to serve as anorectic agents.

The CCK-B or gastrin receptors are found in peripheral neurons, gastrointestinal smooth muscle and gastrointestinal mucosa, most notably in parietal cells, ECL cells, D cells and chief cells. CCK-B receptors also predominate in the brain and have been implicated in the regulation of anxiety, arousal and the action of neuroleptic agents.

U.S. Pat. No. 4,988,692, to Gasc, et al. describes a group of 3-acylamino 1-alkyl-5-phenyl 1,5-benzodiazepine derivatives which behave as cholecystokinin antagonists to reverse or block the effects of the endogenous hormone at its receptors.

U.S. Pat. No. 4,490,304 and PTC applications No's WO90/06937 and WO91/19733 describe peptide derivatives that exhibit CCK-A agonist activity. Such compounds have been disclosed for appetite regulation as well as the treatment and/or prevention of gastrointestinal disorders or disorders of the central nervous in animals and, more particularly, humans.

U.S. Pat. No. 5,187,154 which is incorporated herein by reference describes the use of the neuropeptide cholecystokinin (CCK) to control gastric emptying in patients having an early non-insulin-dependent diabetic condition and exhibiting rapid gastric emptying. Further the specification teaches that compounds which inhibit gastric emptying may be useful to alleviate or eliminate symptoms associated with early or pre-diabetes. Particular symptoms include elevated blood glucose and insulin levels, insulin resistance, increased susceptibility to infection or glycosuria while also maintaining gastric emptying within normal levels.

We have now discovered a novel group of 5-heterocyclo-1,5-benzodiazepine derivatives which exhibit an agonist activity for the CCK-A receptor thereby enabling them to modulate the hormones gastrin and cholecystokinin (CCK) in mammals. Certain of these compounds also exhibit antagonist activity at CCK-B receptors.

The present invention thus provides compounds of the general Formula (I)

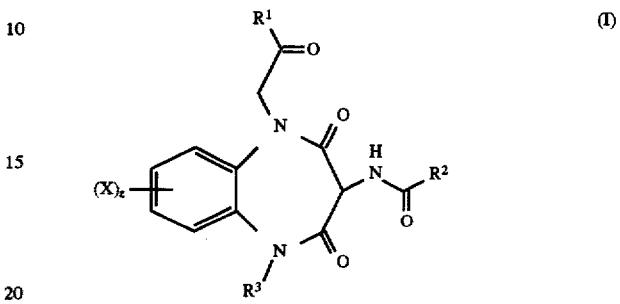

and physiologically salts and solvate thereof wherein
X is either hydrogen, trifluoromethyl, alkyl, $C_{1-4}$alkylthio, —$O(C_{1-4}$alkyl) or halogen;
$R^1$ is either Formula II or —$NR^4R^5$.;

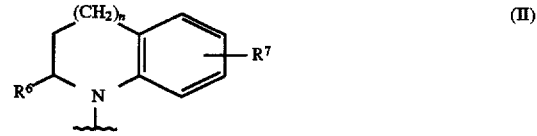

$R^2$ is either:
(1) a heterocycle linked at its 2- position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxobenzopyran may optionally be substituted in the benzo ring thereof by the group $R^9$ as defined hereunder or
(2) phenyl or phenyl mono- or disubstituted independently with halogen, hydroxy, cyano, carboxy, —$O(C_{1-4}$alkyl), —$O(CH_2C_6H_5)$, —$COO(C_{1-4}$alkyl), amino, dimethylamino, —$NHR^{10}$, 1-pyrrolidinyl or tetrazolyl; or
(3) pyridine or pyridinyl mono- or disubstituted independently with halogen, methyl, hydroxy, nitro, cyano, carboxy, —$O(C_{1-4}$ alkyl), —$O(CH_2C_6H_5)$, —$COO(C_{1-4}$alkyl), amino or dimethylamino; or
(4) —$NHR^{11}$ where $R^{11}$ is defined hereinunder or $R^{11}$ is 7-indazolyl containing a group $R^{10}$ at the N-1 position;

$R^3$ is a heterocyclic group (attached to the rest of the molecule via a carbon atom ring member thereof), selected from pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazole, pyrrolidinyl, piperidinyl, morpholinyl or thiomorpholinyl which heterocyclic groups may be substiuted with up to 3 substituents which may be the same or different and selected from halogen, $C_{1-4}$alkyl, nitro, carboxyl, $C_{1-4}$alkoxycarbonyl, $C_{1-4}$alkoxy, $C_{1-4}$alkylthio, amino, $C_{1-4}$alkylamino or di($C_{1-4}$alkyl)amino.

R⁴ is independently C₃₋₆alkyl, C₃₋₆cycloalkyl, C₃₋₆alkenyl, phenyl, —(CH₂)ₚCN or —(CH₂)ₚCOO (C₁₋₄alkyl) and R⁵ is independently C₃₋₆alkyl, C₃₋₆cycloalkyl, C₃₋₆alkenyl, benzyl, phenyl or phenyl mono- or disubstituted independently with C₁₋₃alkyl optionally substituted by one or more fluorine atoms, cyano, hydroxy, dimethylamino, —O(C₁₋₄alkyl), —O(CH₂C₆H₅), —NH(C₁₋₄alkyl), —COO(C¹⁻⁴alkyl), —N(C₁₋₄alkyl)₂ pyrrolidino, morpholino or halogen or R⁴ is C₁₋₂alkyl and R⁵ is phenyl substituted at the 2- or 4- position with chloro, methyl, methoxy or methoxycarbonyl;

R⁶ is hydrogen or methyl;

R⁷ is hydrogen, hydroxy, fluoro, dimethylamino, —O(C₁₋₄alkyl) or —O(CH₂C₆H₅);

R⁸ is —(CH₂)ᵦCOOH;

R⁹ is methyl, chloro, nitro, hydroxy, methoxy or —NHR¹⁰;

R¹⁰ is hydrogen, acetyl, C₁₋₄alkyl, —SO₃H, —SO₂CH₃, —SO₂CF₃ or —SO₂C₆H₅, C₁₋₄alkoxycarbonyl;

R¹¹ is phenyl or phenyl mono- or disubstituted independently with fluorine, trifluoromethoxy, C₁₋₄alkylthio, —(CH₂)𝒸COOH, —(CH₂)𝒸COO(C₁₋₄alkyl), —(CH₂)𝒸SCH₃, —(CH₂)𝒸SOCH₃, —(CH₂)𝒸SO₂CH₃, —(CH₂)𝒸CONH₂, —SCH₂COOH, —CONH(SO₂CH₃), —CONH(SO₂CF₃), —(CH₂)𝒸N(C₁₋₄alkyl)₂, —(CH₂)𝒸NH(SO₂CF₃), —(CH₂)𝒸N(SO₂CF₃)(C₁₋₄alkyl), —(CH₂)𝒸SO₂NHCO(C₁₋₄alkyl), —(CH₂)𝒸SO₂N(C₁₋₄alkyl)CO(C₁₋₄alkyl), —(CH₂)𝒸CONHSO₂(C₁₋₄alkyl), —(CH₂)𝒸CON(C₁₋₄alkyl)SO₂(C₁₋₄alkyl), —(CH₂)𝒸OR¹²—(CH₂)𝒸NHR¹⁰ or phenyl monosubstituted with —(CH₂)𝒸(tetrazolyl), —(CH₂)𝒸(carboxamidotetrazolyl) or —(CH₂)𝒸(pyrrolidinyl) or R¹¹ is selected from pyridine or pyridinyl mono- or disubstituted independently with halogen, methyl, hydroxy, nitro, cyano, carboxy, —O(C₁₋₄ alkyl), amino, dimethylamino, —NHR¹⁰;

R¹² is hydrogen, C₁₋₆alkyl, C₃₋₆cycloalkyl, —CH₂C₆H₅, —CH₂COOH, —CH₂CONH₂, —CH₂CONH(C₁₋₄alkyl), —CH₂CON(C₁₋₄alkyl)₂ or —(CH₂)𝓏CO—N⟨ ⟩O  or

—(CH₂)𝓏CO—N⟨ ⟩N—R¹⁰ z is 1 or 2;

n is 1 or 2;

p is an integer from 1–4;

b is an integer from 0–3; and c is 0 or 1.

When R¹ represents the group of Formula (II), examples of such a group include those wherein R⁶ is hydrogen or more particularly methyl, R⁷ is hydrogen, hydroxyl, methoxy, or fluorine, and n is 1.

When R¹ represents the group NR⁴R⁵, examples of suitable groups include those wherein R⁴ represent C₃₋₆ alkyl, such as propyl or isopropyl, cyclohexyl or phenyl and R⁵ represents C₃₋₆ alkyl, benzyl or phenyl optionally substituted in the para-position by hydroxy, dimethylamino methoxy, trifluoromethyl, fluorine, pyrrolidino or morpholino. Within this group, particularly useful R¹ groups include those wherein R⁴ is propyl and, more particularly, isopropyl and R⁵ represents phenyl or phenyl substituted in the para-position by groups selected from hydroxy, methoxy dimethylamino, fluorine, or morpholino.

Examples of particularly suitable R¹ groups include those wherein R¹ is the group of Formula (II) wherein R₆ is methyl, n is 1 and R⁷ is hydrogen, hydroxy, fluorine or methoxy or R¹ is the group NR⁴R⁵ wherein R⁴ is propyl or isopropyl and R⁵ is phenyl optionally substituted in the para position by a group selected from hydroxy, methoxy, fluoro, dimethylamino, pyrrolidino or morpholino. A particularly interesting R¹ group is that wherein R⁴ is isopropyl and R⁵ is 4-methoxyphenyl When R² represents a group selected from indole, indoline, benzofuran, benzothiophene, quinoline or 4-oxobenzopyran, the optional substituent R⁹ is conveniently a group selected from hydrogen, methyl, methoxy, hydroxy, nitro or amino and, where appropriate, the optional substituent on nitrogen, (R⁸), is —CH₂CO₂H.

When R² is an optionally substituted phenyl group, this is conveniently phenyl or phenyl substituted by one or two groups, which may be the same or different and selected from chlorine, fluorine, amino, hydroxy or carboxyl.

When R² represents the group NHR¹¹, R¹¹ is conveniently phenyl (optionally substituted by fluoro, hydroxy, amino, dimethylamino, trifluoromethylsulphonylamino, C₁₋₄ alkoxycarbonyl, carboxy, 1H-tetrazol-5-yl, acetylamino or OR¹² wherein R¹² represents hydrogen, methyl, benzyl, CH₂CO₂H, CH₂CONH₂, CH₂CONHCH₃, CH₂CON(CH₃)₂

CH₂CON⟨ ⟩O,  CH₂CON⟨ ⟩NH or

CH₂CON⟨ ⟩NCO₂C(CH₃)₃)

or a 7-indazolyl group wherein the N–1 substituent, (R¹⁰), is hydrogen.

When R¹¹ is a mono substituted phenyl group, the substituted is conveniently in the meta-position.

Examples of particularly suitable R² groups includes indole, benzofuran, thiophene, benzothiophene, indoline, quinoline, 4-oxobenzopyran, an optionally substituted phenyl group or the group NHR¹¹. Conveniently, R² is selected from the group indole, indoline or benzofuran, an optionally substituted phenyl group or the group NHR¹¹. More particularly, R² represents an indole, an optionally substituted phenyl or NHR¹¹.

When R³ represents pyridyl examples of suitable groups including 2-pyridyl, 3-pyridyl and 4-pyridyl.

When R³ represents pyrimidinyl example of suitable groups include 2-pyrimidinyl, or 5-pyrimidinyl.

When R³ represents pyrazolyl examples of suitable groups include 1,3,5-trimethyl-1H-pyrazole-4-yl.

Examples of particularly suitable R³ groups include pyridyl e.g. 2-pyridyl, 3-pyridyl, 4-pyridyl, pyrimidinyl e.g. 2-pyrimidinyl, or 5-pyrimidinyl or 1,3,5-trimethyl-1H-pyrazol-4-yl.

A particularly useful group of compounds according to the invention include those wherein R¹ represents the group NR⁴R⁵ wherein R⁴ is propyl or isopropyl and R⁵ is phenyl optionally substituted in the para position by a group selected from hydroxy, methoxy, fluoro, dimethylamino or monopholino; $R^2$ represents phenyl (optionally substituted independently by one or two groups selected from chlorine, fluorine, hydroxy, amine or carboxy), $NHR^{11}$ wherein $R^{11}$ represents phenyl (optionally substituted by amino, dimethylamino, trifluoromethyl-sulphonylamino, carboxy, 1H-tetrazo-5-yl, acetylamino or $OR^{12}$ wherein $R^{12}$ represents hydrogen, methyl, benzyl, $CH_2CO_2H$, $CH_2CONH_2$, $CH_2CONHCH_3$, $CH_2CON(CH_3)_2$,

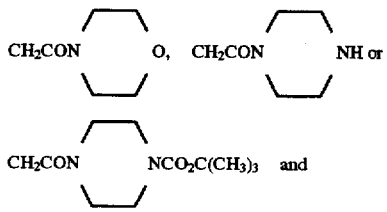

wherein the substituent is preferably in the meta-position) or an indole wherein the nitrogen atom is optionally substituted by the group —$CH_2CO_2H$ and the benzo ring is optionally substituted by chlorine, methyl, methoxy, nitro, hydroxy or amino; $R^3$ represents pyridyl e.g. 2, 3 or 4 pyridyl, pyrimidinyl e.g. 2 or 5 pyrimidinyl or 1,2,5-trimethyl-1H-pyrazol-4-yl and X is hydrogen or fluorine.

A particularly interesting class of compounds of the present invention which exhibits a very high and selective affinity for the CCK-A receptor as well as exceptional efficacy occurs wherein $R^2$ is an indole group. A preferred group of compounds within this class are those wherein the indole group is substituted on the nitrogen atom by the group —$CH_2CO_2H$ or, more preferably, the nitrogen atom is unsubstituted, and benzo ring of the indole group is optionally substituted by a group selected from chlorine, methyl, methoxy, nitro, hydroxy or amino. Within this group especially useful compounds are those wherein $R^4$ represents isopropyl, $R^5$ represents p-methoxy phenyl and $R^3$ represents pyridyl, pyrimidinyl or 1,3,5-triemethyl-1H pyrazol-4-yl or more particularly $R^3$ represents 3-pyridyl and X represents hydrogen.

Preferred compounds of the invention include:
1H-Indole-2-carboxylic acid {1-[Isopropyl-(4-methoxyphenyl)-carbamoylmethyl]-2,4-dioxo-5-pyridin-2-yl-2,3,4,5-tetrahydro-1H-benzo[b][1,4]diazepin-3-yl}-amide;
1H-Indole-2-carboxylic acid {1-[Isopropyl-(4-methoxyphenyl)-carbamoylmethyl]-2,4-dioxo-5-pyrimidin-2-yl-2,3,4,5-tetrahydro-1H-benzo[b][1,4]diazepin-3-yl}-amide;
2-[2,4-Dioxo-3-(3-phenyl-ureido)-5-pyridin-2-yl-2,3,4,5-tetrahydrobenzo[b][1,4]diazepin-1-yl]-N-isopropyl-N-(4-methoxy-phenyl)-acetamide and enantiomers thereof.

A particularly preferred compound of the invention is 1H-Indole-2-carboxylic acid {1[isopropyl-(4-methoxyphenyl)-carbamoylmethyl]-2,4-dioxo-5-pyridin-3-yl-2,3,4,5-tetrahydro-1H-benzo[b][1,4]diazepin-3-yl}-amide; and enantiomers thereof.

As provided herein, the term alkyl is generally intended to mean both straight chain and branched chain aliphatic isomers of the corresponding alkyl. For example, $C_{1-6}$alkyl is intended to include methyl, ethyl, n-propyl, isopropyl, n-butyl, isobutyl, tertbutyl, n-pentyl, etc.

The term cycloalkyl, as provided herein, is intended to mean all alicyclic isomers of the corresponding alkyl. For example, the term $C_{3-6}$ alkyl, as provided herein, is intended to include such groups as cyclopropyl, cyclopentyl and cyclohexyl.

The term halogen is intended to mean F, Cl, Br or I.

The term tetrazole as a group or part of a group refers to the (10H)-tetrazol-5-yl grouping and tautomers thereof.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of Formula (I) include conventional salts formed from pharmaceutically acceptable inorganic or organic acids as well as quaternary ammonium acid addition salts. More specific examples of suitable salts include hydrochloric, hydrobromic, sulphuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulphonic, methanesulphonic, naphthalene-2-sulphonic, benzenesulphonic and the like. Other acids such as oxalic, while not in themselves pharmaceutically acceptable, may be useful in the preparation of salts useful as intermediates in obtaining the compounds of the invention and their pharmaceutically acceptable salts. References hereinafter to a compound according to the invention include both compounds of Formula (I) and their pharmaceutically acceptable salts and solvates.

The compounds of the present invention exhibit CCK-A agonist activity and can be considered full or partial cholecystokinin agonists in that they bind to CCK-A receptors and either fully or partially stimulate gallbladder contraction and/or reduce feeding in animal paradigms.

As agonists of CCK-A receptors, the compounds of the present invention are useful anorectic agents advantageous in the treatment of obesity as well as related pathologies, such as diabetes or hypertension. Moreover, the compounds disclosed herein provide for new approaches for inducing satiety, providing for appetite regulation and modifying food intake in mammals, especially humans, to regulate appetite, treat obesity and maintain weight loss. The compounds are also useful for the treatment of non-insulin dependent diabetic conditions associated with rapid gastric emptying.

Additionally, certain compounds of the present invention may also exhibit some antagonist activity at particular site-specific CCK-B and gastrin receptors as demonstrated by their inhibition of CCK-4 stimulated contraction of isolated guinea-pig ileum longitudinal muscle-myenteric plexus and pentagastrin-stimulated acid secretion in rat isolated gastric mucosa using the procedures described by M. Patel and C. F. Spraggs in Br. J. Pharmac., (1992), 106, 275–282 and by J. J. Reeves and R. Stables in Br. J. Pharmac., (1985), 86, 677–684.

The relative affinities of compounds of the invention for the CCK-A and CCK-B receptors may be determined using known conventional procedures such as described by Fornos et al J. Pharmacol Exp. Ther., 1992 261, 1056–1063.

The ability of compounds of the invention to inhibit gastric acid secretion, such as pentagastrin stimulated acid secretion may be determined in the conscrious gastric fistula rat using methods described by Hedges and Parsons Journal of Physiology 1977, 267 191–194.

The compounds of formula (I) inhibit or delay gastric emptying and this may be determined using standard tests. Thus for example rats deprived for food for 18 hr may be pretreated with the test compound administered i.p at a pre-set time (20 mins) before being given a methyl cellulose meal which is administered by the gavage route. The meal contains a marker element such as Phenol Red. After specific predetermined time intervals the rats are sacrificed and the amount of the meal in the stomach is determined by measuring the concentration of the marker substance present. This value is then compared with a control animal which was not pre-treated with the test compound.

Compounds of the invention have been found to have a particularly advantageous profile of activity in terms of good oral bioavailability coupled with relatively good water solubility.

In particular, the invention provides a compound of Formula (I) or a pharmaceutically acceptable salt or solvate thereof for use in therapy, and in particular, in human medicine.

According to another aspect, the present invention provides the use of a compound of Formula (I) or a pharmaceutically acceptable salt or solvate thereof for the manufacture of a medicament for the treatment of conditions where modification of the effects of CCK and/or gastrin is of therapeutic benefit.

According to a further aspect of the present invention, there is provided herein a method for the treatment of a mammal, including man, in particular in the treatment conditions where modification of the effects of CCK and/or gastrin is of therapeutic benefit, the method comprising administering to the patient an therapeutically effective amount of a compound of Formula (I) or a pharmaceutically acceptable salt or solvate thereof.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of Formula (I) or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Formulations of the present invention include those especially formulated for oral, buccal, parenteral, implant, or rectal administration, however, oral administration is preferred. For buccal administration, the composition may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art. Suitable tablet coatings include conventional enteric coatings.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

For oral administration the compounds of the invention are conveniently administered as enteric coated tablets or capsules made from enteric materials or coated with an enteric film.

Additionally, compositions the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The composition according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The compositions according to the invention may contain between 0.1–99% of the active ingredient, conveniently from 30–95% for tablets and capsules and 3–50% for liquid preparations.

Compounds of general formula (I) and salts thereof may be prepared by the general methods outlined hereinafter. In the following description, the groups $R^1$–$R^{12}$ and X are as defined for the compounds of formula (I) unless otherwise stated or may be groups convertible thereto.

Thus for any of these processes, it may be necessary and/or desirable to protect sensitive or reactive groups. Protecting groups are employed according to standard methods of organic synthesis (T. W. Green and P. G. M Watts (1991) *Proecting Groups in Organic Synethesis*, John Wiley & Sons). These groups are removed at a convenient stage of synthesis using methods known from the art. Thus, for example, amino groups may be protected by a group selected from arylmethyl (e.g. benzyl), acyl, or sulfonyl, e.g. allylsulfonyl, phthalimide, or tosyl; subsequent removal of the protecting group being effected when desired by hydrolysis or hydrogenolysis as appropriate using standard conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl or methoxymethyl, arylmethyl e.g. benzyl, diphenylmethyl, or triphenylmethyl, heterocyclic groups such as tetrahydropyranyl, acyl e.g. acetyl or benzoyl and silyl groups such as trialkylsily, e.g. tertbutyldimethylsily. The hydroxyl protecting groups may be removed by conventional techniques. Thus, for example, alkyl, silyl acyl, and heterocyclic groups may be removed by hydrolysis under acidic or basic conditions. Arylmethyl groups such as triphenylmethyl may similarly be removed by hydrolysis under acidic conditions. Aralymethyl groups such as benzyl may be cleaved by hydrogenolysis in the presence of a Nobel metla catalyst such as passadium-on-charcoal. Silyl groups may also conveniently be removed using a source of fluoride ions such as tetra-n-butylammonium fluroride.

According to a first general process A, compounds of formula (I) may be prepared by the reaction of an amine of formula (III) wherein $R^1$, $R^2$, $R^3$, X and z have the meanings defined in formula (I)

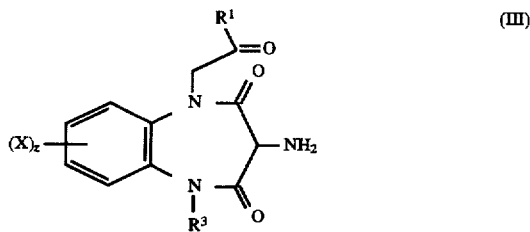

(III)

with a compound $R^{11}Y$ (IV) wherein Y is the group —NCO, HNCOCl or NHCOR$_a$ where R'$_a$ is nitro substituted phenoxy group or a 1-imidazole group.

The reaction conveniently takes place in the presence of a suitable solvent such as a halohydrocarbon (e.g. dichloromethane), an ether (e.g. tetrahydrofuran) or nitrile (e.g. acetonitrile) or a mixture thereof at a temperature in the range of 0°–80° C.

Compounds of formula (IV) wherein Y is —NCO) may be purchased or prepared by the reaction of amines H$_2$N—R$^{11}$ with phosgene or triphosgene in a suitable solvent such as methylene chloride. Compounds of formula (IV) wherein Yis NHCOCl are also prepared by the reaction of amines H$_2$NR$^{11}$ with phosgene or triphosgene in a suitable solvent such as methylene chloride. Compounds of formula (IV) wherein Y is NHCOR$_a$ and R$_a$ is a 1-imidazole group are prepared by treatment of amines H$_2$N—R$^{11}$ with carbonyl diimidazole in a suitable solvent (dichloromethane, ether, tetrahydrofuran) at a temperature ranging from 0°–80° C. (conveniently at room temperature). Compounds of formula (IV) wherein Y is HNCOR$_a$ and R$_a$ is a nitro substitued phenxoy group are prepared by the reaction of amines H$_2$N—R$^{11}$ with the appropriate chloroformate R$_a$COCl in the presence of a base (pyridine, triethylamine) in a suitable solvent (dichloromethane) and at a temperature of 0°–50° C.

According to a further general process B, compounds of formula (I) may be prepared by reaction of an intermediate of formula (V).

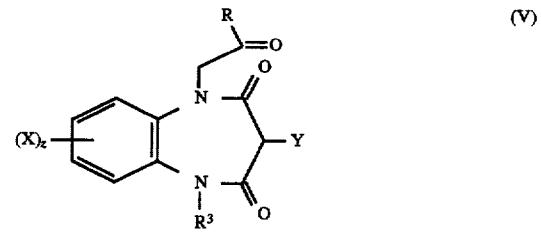

(V)

wherein Y is the group —NCO, —NHCOCl or NHCOR$_a$ wherein R$_a$ is a nitro substituted phenoxy group or a 1-imidazole group with an amine (VI)

$$H_2N—R^{11}$$ (VI)

and optionally in the the presence of a base such as a tertiary amine (e.g. triethylamine).

The reaction conveniently takes place in a suitable solvent such as a halogenated hydrocarbon (e.g. dichloromethane) or an ether (e.g. tetrahydrofuran) or an amide (e.g. N,N-dimethyl formamide) optionally at a temperature ranging from room temperature to the reflux temperature of the solvent.

Conveniently the compounds of formula (V) are prepared in situ from the amine (III).

In a particular aspect of the process (B) when Y is the group NHCOR$_a$ and R$_a$ is a 1-imidazole group, the imidazolide (V) may be formed in situ in which case the amine of formula (VI) will be mixed with the compound of formula (III)

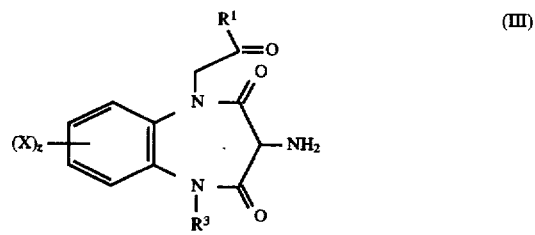

(III)

in the presence of carbonyldiimidazole under the aforementioned conditions.

For process B when Y is the group NHCOR$_a$ and R$_a$ is a nitro substituted phenoxy group the reaction with the primary amine (VI) is preferably carried out in the presence of a base such as a tertiary amine e.g. triethylamine.

For process B when Y is the isocyanate group —N=C=O the reaction with the primary amine (VI) is preferably carried out in an aprotic solvent such as a halohydrocarbon e.g. methylene chloride. Conveniently the isocyanate is generated in situ prior to the addition of the primary amine (VI).

The compounds of formula (V) wherein R$_a$ is an optionally substituted phenoxy group may be prepared from the primary amine (III) by reaction with the corresponding nitro substituted phenyl chloroformate in the presence of a base such as pyridine. The reaction may be carried out in a solvent such as a halohydrocabon e.g. dichloromethane and at a temperature from 0°–500°.

Compounds of formula (V) wherein R$_a$ is a 1-imidazole group may be prepared by reacting a compound of formula (III) with carbonyldiimidazole in the presence of a suitable solvent such as a halogenated hydrocarbon (e.g. dichloromethane) or an ether (e.g. tetrahydrofuran) at a temperature ranging from 0° to 80° (conveniently at room temperature).

Compounds of formula (V) wherein Y is the isocyanate grouping —N=C=O or carbamoyl chloride —NHCOCl may be prepared from the primary amine (III) by reaction with phosgene (COCl$_2$) or triphosgene in a suitable solvent such as methylene chloride.

According to a further general process C compounds of formula (I) may also be prepared by a reaction of the compound of formula (VII)

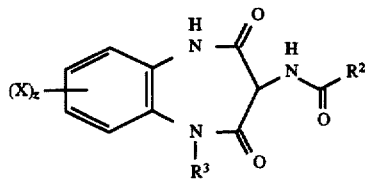
(VII)

with a haloacetamide having the formula (VIII)

  (VIII)

wherein hal=Cl or Br.

The reaction is conveniently carried out by treating the compound of formula (VII) with a strong base such as sodium hydride in a polar aprotic solvent such as N,N-dimethylformamide followed by reaction with the acetyl halide (VIII).

The acetyl halide (VIII) is prepared by the reaction of the amine R$^1$—H with corresponding haloacetyl bromide in dichloromethane at 0° C., with a suitable base, such as triethylamine.

The amines R$^1$—H wherein R$^1$ is the group —NR$^4$R$^5$, may be prepared by the reductive alkylation of the amine H$_2$N—R$^5$ with an appropriate aldehyde or ketone.

According to general process D, compounds of general Formula (I) may also be prepared by the reaction of the intermediate of Formula (III) with acids of Formula (IX), as set forth below.

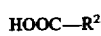  (IX)

Thus reaction of the intermediates of formula (III) with the acid of formula (IX) may be carried out in the presence of a suitable dehydrating agent such as dicyclohexylcarbodiimide (DCC), 1(-3-dimethylaminopropyl)-3-ethylcarbodiimide hydrochloride (EDC) or 4-benzotriazol-1-yloxytris-(dimethylamino)phosphonium hexafluorophosphate (BOP, particularly in the presence of a suitable alcohol (N-hydroxylsuccinimide or N-hydroxybentriazole).

Alternatively, compounds of general Formula (I) may be obtained by reaction of the intermediates of Formula (III) with an activated derivative of the acid (IX) such as an acid chloride or anhydride thereof, including mixed anhydrides.

Preferred solvents for general process D include N,N-dimethylformamide or dichloromethane. Preferred temperatures are between 0°–60° C. Preferred bases for this reaction include triethylamine N-methylmorpholine or N,N-dimethylaminopyrine (DAMP).

According to a further general process (E) compounds of formula (I) may be prepared by reaction of a compound corresponding to a compound of formula (I) wherein R$^3$ represents hydrogen with the halide R$^3$ hal (wherein hal is Cl or Br and R$^3$ is a group as defined in formula (I) and more particular a heteroaryl group e.g. pyridyl, pyrimidinyl etc). The reaction is conveniently carried out in the presence of copper metal and potassium acetate and in the presence of a solvent such as dimethylsulphoxide or N,N-dimethylformamide and preferably the reaction is carried out at a temperature within the range 25°–100° C.

According to a further general process (F) compounds of the invention may be converted into other compounds of the invention. Thus for example compounds of formula (I) wherein R$^8$ is the group (CH$_2$)$_b$CO$_2$H may be prepared by reaction of a compound of formula (I) wherein R$^8$ is hydrogen with compound Br(CH$_2$)$_b$COOR* wherein R* is C$_{1-4}$alkyl in the presence of a strong base such as sodium hydride followed by removal of the carboxy protecting group by conventional procedures e.g. acidic or basic hydrolysis Also compounds of formula (I) in which R$^{11}$ is phenyl substituted by an alkoxy carbonyl group may be hydrolysed by conventional means, e.g. acid hydrolysis to give a compound of formula (I) in which R$^{11}$ is phenyl substituted by carboxy.

Compounds of formula (III) may be prepared by reduction of compounds of formula (X)

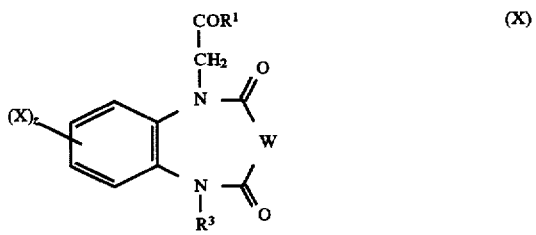  (X)

wherein

W is CH—N$_3$ or C=N—NHPh.

Compounds of formula (X) wherein W is CH—N$_3$ may be reduced to a compound of formula (III) by hydrogenation in the presence of a suitable catalyst such as 5–10% palladium on a support such as carbon or calcium carbonate, or platinum (IV) oxide. The reaction conveniently takes place in the presence of a solvent such, as an alkanol (e.g. ethanol) an ester (e.g. ethyl acetate) or acetic acid.

Compounds of formula (X) wherein W is C=N—NHPh may be reduced to a compound of formula (III) by reaction with zinc and acetic acid. This reaction may be carried out a temperature with the range 0°–500°.

Compounds of formula (X) wherein W is CHN$_3$ may be prepared from a compound of formula (X) wherein W is CH$_2$ by treatment with a strong base such as sodium hydride or potassium hexamethyl disilazide or potassium tert-butoxide followed by tri-isopropyl benzenesulphonyl azide or di-tertbutoxyazidodicarboxylate. The reaction conveniently takes place in a solvent such as an ether (e.g., tetrahydrofuran) at a temperature in the range of −78° to 20°.

Compounds of formula (III) may also be prepared by reaction of a compound of formula (X) wherein W is CH$_2$ with a suitable base such as sodium his (trimethylsilyl) amide and O-(diphenyl-phosphenyl) hydroxylamine in a solvent such as dimethyl formamide.

Compounds of formula (X) in which W is C=NNHPh or CH$_2$ may be prepared by reaction of the ortho-phenylenediamine (XI) with the diacid chloride (XII) wherein Q is CH$_2$ or C=NNHPh, in a suitable solvent such as an ether e.g. tetrahydrofuran

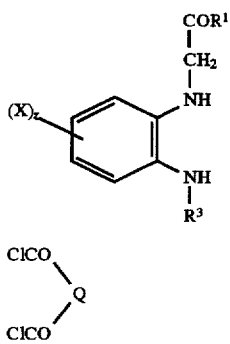

(XI)

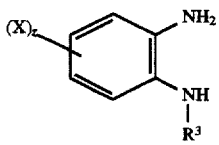

(XII)

The compound of formula (XII) wherein Q is C=NNHPh may be prepared by reaction of ketomalonic acid with phenyl hydrazone followed by reaction with phosphorus pentachloride.

Compounds of formula (XI) are either known compounds or may be prepared by analogous methods. Thus for example a compound of formula (XI) may be prepared by alkylation of the amine (XIII).

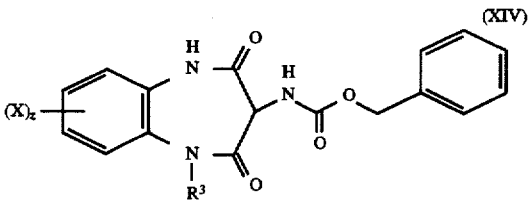

(XIII)

Thus the amine (XIII) may be reacted with the compound $R_1COCH_2$hal wherein hal is chlorine or bromine, optionally in the presence of sodium iodide in a solvent such as N,N-dimethylformamide and a base such as potassium carbonate.

An alternative preparation of the intermediate of Formla (III) as set forth below, involves treatment of the intermediate of Formula (XIV) with sodium hydride followed by addition of a haloacetamide (VIII) in a suitable solvent, such as N,N-dimethyl formamide, at 0° C. to provide the protected intermediate of Formual (XV)

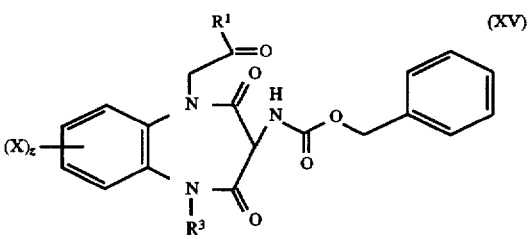

(XIV)

(XV)

Intermediate (XVI) may be converted to amine (III) by treatment with HBr in methylene chloride.

Intermediate (XIV) is obtained from the intermediate of Formula (XVI) by reaction with benzyloxychloroformate in dichloromethane, using triethylamine as base. This reaction is run conveniently at room temperature.

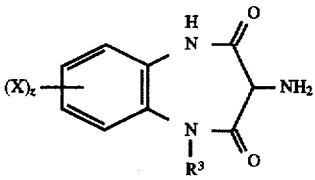

(XVI)

Intermediate (XVI) is prepared from phenylene diamine (XIII) by the following process.

Reaction of the diamine (XIII) with p-methoxybenzoylchloride followed by reduction of the amide thus formed with lithium aluminum hydride yields the N-protected diamine (XVII)

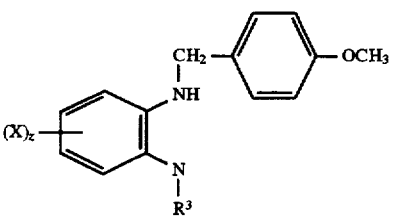

(XVII)

Reaction of compound (XVII) with the diacid chloride (XII; Q=C=NNHPh) followed by reduction with zinc and acetic acid yields the amine (XVIII)

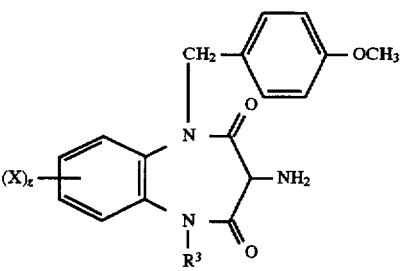

(XVIII)

The compound of formula (XVIII) may be converted into the required compound (XVI) by rection with $Ce(NO_2)_6NH_4$ (ceric ammonium nitrate).

Compounds of formula (VII) may be prepared from a compound of formula (XVI) using the general processes A, B or C. described above.

Compounds corresponding to those of formula (I) but wherein $R^3$ represents hydrogen may be prepared from the corresponding amine (III) wherein $R^3$ represents hydrogen using the general processes A , B and C. Compounds of formula (III) wherein $R^3$ is hydrogen may be prepared using the general processes described above for preparing compounds of formula (III) wherein $R^3$ is a heterocyclic group but using intermediates wherein $R^3$ is a p-methoxybenzyl group which can then be removed in a conventional manner.

Thus reaction of the diamine (XIX)

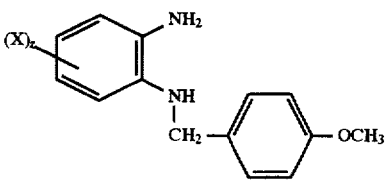

(XIX)

with the haloacetamide (VIII) yields the disubstituted diamine (XX)

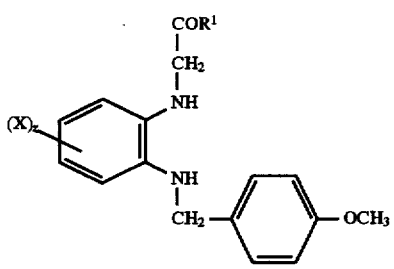

Reaction of compound (XX) with the diacid chloride (XII) wherein Q is C=NNHPh, followed by reduction with zinc and acetic acid yields the benzodiazepine (XIX)

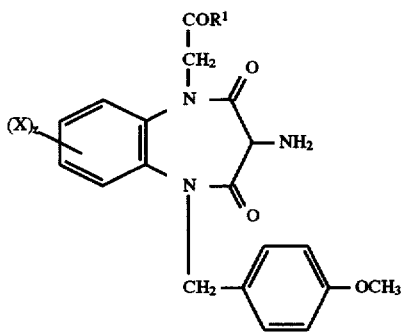

Reaction of the compound of formula (XXI) with ceric ammonium nitrate yields the compound corresponding to that of formula (III)wherein $R^3$ is hydrogen.

The diamine (XIX) may be prepared by reaction of the nitro fluro derivative (XXII)

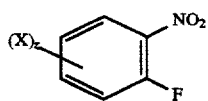

with p-methoxybenzylamine followed by reduction of the nitro group.

Compounds of formula (X) wherein W is $CH_2$ may be prepared by reaction of the compound of formula (XXIII) wherein X, z and $R^1$ have the meanings defined in formula (I)

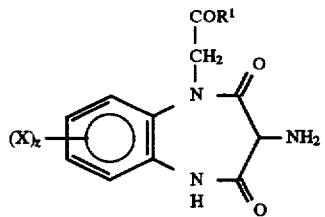

With the bromide $R^3$ Br (wherein $R_3$ has the meaning defined above) in the presence of copper dust and potassium acetate. The reaction is preferably carried out in a polar solvent such as dimethylformamide and with heating.

The compound (XXIII) may be prepared by reaction of the diamine (XXIV) wherein $X_1$, z and $R^1$ have the meanings defined above.

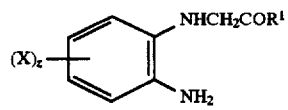

with malonyl dichloride in a similar matter to that described for the preparation of a compound of formula (X) wherein W is $CH_2$.

Compounds of formula (I) contain at least one asymmetric carbon atom, namely the carbon atom of the diazepine ring to which the substituted urea grouping is attached. Specific enantiomers of the compounds of formula (I) may be obtained by resolution of the racemic compound using conventional procedures such as chiral HPLC. Alternatively the required enantiomer may be prepared from the corresponding enantiomeric amine of formula (III) using any of the processes described above for preparing compounds of formula (I) from the amine (III). The enantiomers of the amine (III) may be prepared from the racemic amine (II) using conventional procedures such as salt formation with a suitably optically active acid or by preparative chiral HPLC.

EXAMPLES

The following examples are set forth to illustrate the synthesis of some particular compounds of the present invention and to further exemplify particular applications of general process A-E. Accordingly, the following Example section is in no way intended to limit the scope of the invention contemplated herein.

As used herein the symbols and conventions used in these processes, schemes and examples are consistant with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); psi (pounds per square inch); M (molar); mM (millimolar); i.v. (intravenous); Hz (Hertz); mol (moles); RT (room temperature); min (minutes); h (hours); M.p. (melting point); TLC (thin layer chromatography); MeOH (methanol); TFA (trifluoroacetic acid); THF (tetrahydrofuran); dimethylsulfoxide (DMSO); EtOAc (ethyl acetate); dichloromethane (DCM); dimethylformamide (DMF); 1,1-carbonyldiimidazole (CDI); isobutylchloroformate (iBuCF); N-hydroxysuccinimide (HOSu); N-hydroxybenztriazole (HOBT); 1-(3-dimethylaminopropyl)-3-ethylcarbodiimide hydrochloride (EDC); bis(2-oxo-3-oxazolidinyl) phosphinic chloride (BOP); tert-butyloxycarbonyl (BOC); dicyclohexylcarbodiimide (DCC); benzyloxycarbonyl (Cbz). DMAP 4-dimethylaminopyridine. All references to ether are to diethyl ether. Unless otherwise indicated, all temperatures are expressed in °C. (degrees Centigrade). All reactions conducted at room temperature unless otherwise noted.

The $^1$HNMR spectra were recorded on either a Varian VXR-300 or a Varian Unity-300 instrument. Chemical shifts are expressed in parts per million (ppm, d units). Coupling constants are in units of hertz (Hz). Splitting patterns are designated as s, singlet; d, doublet; t, triplet; q, quartet; m, multiplet; b, broad.

Low-resolution mass spectra (MS) were recorded on a JOEL JMS-AX505HA, JOEL SX-102 or a SCIEX-APIiii spectrometers. All mass spectra were taken in the positive ion mode under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid or p-anisldehyde solution. Flash column chromatography was performed on silica gel (230–400 mesh, Merck).

Products were purified by preparative reversed phase high pressure liquid chromatography (RP-HPLC) using a Waters Model 3000 Delta Prep equipped with a Delta-pak radial compression cartridge ($C_{18}$, 300 A, 15 m, 47 mm×300 mm). Solvent systems included A, aqueous 0.1% trifluoroacetic acid, B, 60% acetonitrile, 40% aqueous 0.1% trifluoroacetic acid and C, acetonitrile. All solvents contained 0.1% TFA. Linear gradients were used in all cases and the flow rate was 100 mL/minute ($t_0$=5.0 min.). Analytical purity was assessed by RP-HPLC using a Waters 600E system equipped with a Waters 990 diode array spectrometer (I range 200–400 nM). The stationary phase was a Vydac $C_{18}$ column (5 m, 4.6 mm×250 mm). The flow rate was 1.0 to 1.5 ml/min. ($t_0$=2.8 or 3.0 min.) and the solvent systems were as described above. Data reported as tr, retention time in minutes (% acetonitrile over time).

Example 1

2-[2,4-Dioxo-3-(3-phenyl-ureido)-5-pyridin-2-yl-2, 3,4,5-tetrahydrobenzo[b][1,4]diazepin-1-yl]-N-isopropyl-N-(4-methoxy-phenyl)-acetamide A solution of phenyl isocyanate (25.6 mg) in methylene chloride (1 ml) was added to a solution of 2-(3-Amino-2,4-dioxo-5-pyrdin-2-yl-2,3,4,5-tetrahydrobenzo[b][1,4]diazepin-1-yl)-N-isopropyl-N-(4-methoxy-phenyl)-acetamide (100 mg) in methylene chloride (1 ml) and the resultant mixture was stirred at rt for 4 h. The solvents were removed in vacuo and the residue was recrystalised from ethyl acetate to afford the title product (44 mg) as an off-white solid. $^1$H NMR (300 MHz, CDCl$_3$); 1.03 (2×d, J=7 Hz, 6H), 3.81 (s, 3H), 4.17 (d J=16 Hz, 1H), 4.37 (d, J=16 Hz, 1H), 5.0 (sept, J=7.1 Hz, 1H), 5.40 (d, J=6.3 Hz, 1H), 6.40 (d, J=5.3 Hz, 1H), 6.8–7.3 (m, 17H), 7.80 (br, 1H), 8.42 (d, J=3.9 Hz, 1H).Tlc (10% MeOH, CH$_2$Cl$_2$) Rf=0.53. m/z [MH]$^+$=593.

Example 2

1H-Indole-2-carboxylic acid {1-[Isopropyl-(4-methoxy-phenyl)-carbamoylmethyl]-2,4-dioxo-5-pyrdin-2-yl-2,3,4,5-tetrahydro-1H-benzo[b][1,4]diazepin-3-yl}-amide A solution of 2-(3-Amino-2,4-dioxo-5-pyrdin-2-yl-2,3,4,5-tetrahydrobenzo[b][1,4]diazepin-1-yl)-N-isopropyl-N-(4-methoxy-phenyl)-acetamide (276 mg), BOP (244 mg), HOBT (78 mg), DMAP (69 mg) and indole-2-carboxylic acid (98 mg) in DMF (1 ml) was stirred at rt for 18 h. The reaction mixture was diluted with ethyl acetate (15 ml), washed with 1N aqueous sodium hydroxide solution (2×15 ml), water (20 ml), brine (20 ml), dried (K$_2$CO$_3$) and concentrated in vacuo to afford the cude product. Purification by RP-HPLC utilizing a linear gradient (20% A, 80% B to 90% B, 10% C, 30 min) gave the title product (26.6 mg) as a white lyophile;Tr=21.3 min. $^1$H NMR (300 MHz, CDCl$_3$); 0.98 (2×d, J=7 Hz, 6H), 3.68 (s, 3H), 4.17 (d J=16.6 Hz, 1H), 4.37 (d, J=16.8 Hz, 1H), 4.87 (sept, J=6.8 Hz, 1H), 5.40 (d, J =6.8 Hz, 1H), 6.40 (d, J=5.3 Hz, 1H), 6.75–6.84 (m, 5H), 6.92–6.99 (m, 2H), 7.07 (t, J=7.3 Hz, 1H), 7.09–7.2 (m, 4H), 7.24 (t, J=9.2 Hz, 1H), 7.40 (t, J=9.1 Hz, 2H), 7.52 (d J=7.9 Hz, 1H), 7.72 (m, 2H), 8.38 (d, J=4.4 Hz, 1H), 9.19 (s, 1H). m/z [MH]$^+$=617.

Examples 3 and 4

(+) or (−) 1H-Indole-2-carboxylic acid {1-[Isopropyl-(4-methoxy-phenyl)-carbamoylmethyl]-2, 4-dioxo-5-pyridin-2-yl-2,3,4,5-tetrahydro-1H-benzo [b][1,4]diazepin-3-yl}-amide A 100 mg portion of Example 2 was applied to a semi-preparative Pirkle D-Leucine column and the individual enantiomers were eluted with an isocratic solvent system consisting of hexane (77%), isopropyl alcohol (20%) and acetonitrile (3%). Each solvent contained 0.3% diethylamine. Appropriate fractions were collected and combined. The solvent was removed in vacuo and the residue was triturated with water. The resulting precipitate was separated by filtration and dried in vacuo.

Example 3

Chiral analytical (Pirkle D-Leucine, 2 ml/min) tr=19.62 min (100%);

m/z [MH]$^+$=617

Example 4

Chiral analytical (Pirkle D-Leucine, 2 ml/min) tr=22.797 min (98.4%);

m/z [MH]$^+$=617

Example 5

1H-Indole-2-carboxylic acid {1-[Isopropyl-(4-methoxy-phenyl)-carbamoylmethyl]-2,4-dioxo-5-pyrimidin-2-yl-2,3,4,5-tetrahydro-1H-benzo[b][1,4]diazepin-3-yl}-amide To a solution of 2-(3-Amino-2,4-dioxo-5-pyrimidin-2-yl-2,3,4,5-tetrahydro-benzo [b] [1,4]diazepine-1-yl)-N-isopropyl-N-(4-methoxy-phenyl)-acetamide (933 mg, 1.97 mmol) in DMF (20 mL) were added indole-2-carboxylic acid (333 mg, 2.07 mmol), N-hydroxybenzotriazole (266 mg, 1.97 mmol), and 1-(3-dimethylaminopropyl)-3-ethylcarbodiimide hydrochloride (415 mg, 2.16 mmol) successively with stirring at ambient temperature. The resultant mixture was stirred at ambient temperature for 18 hours. The solvent was evaporated under reduced pressure to give a yellow oil which was dissolved in ethyl acetate (100 mL), washed with water (2×30 mL), dried over MgSO$_4$, filtered and concentrated under reduced pressure to a give a tan foam. The crude product was purified by flash chromatography on silica gel (30 g) eluting with ethyl acetate (600 mL). Appropriate fractions were combined and concentrated in vacuo to give the title compound (902 mg, 1.46 mmol) as a white foam: $^1$H NMR (CDCl$_3$, 400 MHz): 9.44 (s 1H), 8.75 (d, 2H, J=4.4 Hz), 7.64–6.88 (m,15H), 5.60 (d, 1H, J=6.8 Hz), 5.03 (m, 1H), 4.45 (d, 1H, J=16.6 Hz), 3.99 (d, 1H, J=16.6 Hz), 3.81 (s, 3H), 1.07 (m, 6H); TLC (CH$_2$Cl$_2$/CH$_3$OH (19:1)): R$_f$=0.63; MS (FAB) m/z 618.2 (MH$^+$).

Example 6

1H-Indole-2-carboxylic acid [1-[isopropyl-(4-methoxy-phenyl)-carbamoylmethyl]-2,4-dioxo-5-(1, 3,5-trimethyl-1H-pyrazol-4-yl)-2,3,4,5-tetrahydro-1H-benzo[b][1,4]diazepin-3-yl]-amide To a solution of 2-[3-Amino-2,4-dioxo-5-(1,3,5-trimethyl-1H-pyrazol-4-yl)-2,3,4,5-tetrahydro-benzo[b][1, 4]diazepin-1-yl]-N-isopropyl-N-(4-methoxy-phenyl)-acetamide (385 mg, 0.76 mmol) in DCM (5 mL) was added indole-2-carboxylic acid (148 mg, 0.92), HOBT (125 mg, 0.92 mmol), EDC (176 mg, 0.92 mmol), and TEA (2d). The solution stirred at RT for 48 h, then poured into DCM (100 mL). The mixture was extracted with saturated sodium bicarbonate (×2), brine, dried over MgSO$_4$, and concentrated in vacuo. The resulting solid was triturated with ethanol to yield the title compound (159 mg): Tr=18.3 min (30–55%C over 30 min); $^1$HNMR (d$_6$-DMSO, 300 MHz) δ

11.8 (s, 1H), 8.45(s, 1H), 7.7–6.9 (m, 12H), 5.36 (m, 1H), 4.78 (m, 1H), 4.23 (m, 2H), 3.79 (s, 3H), 3.64 (d, 3H, J=26.6), 2.11 (d, 3H, J=31), 1.5 (d, 3H, J=72); low resolution MS(FAB) m/e 648 (MH+).

Example 7

1H-Indole-2-carboxylic acid {1[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-amide To a solution of 1H-Indole-2-carboxylic acid {1[isopropyl-(4-methoxy-phenyl)-carbamoylmethyl]-2,4-dioxo-2,3,4,5-tetrhydro-1H-benzo[b][1,4]diazepine-3-yl}amide (0.14 g, 0.26 mmol) and 3-bromopyridine (40 μL, 0.42 mmol)in DMF (1 mL) was added copper powder (46 mg, 0.73 mmol) and acetic acid potassium salt (38 mg, 0.73 mmol). The heterogenous solution was stirred at 100° C. for 15 h and subsequently hot filtered through celite and washed with methanol. The resulting precipitate was filtered and purified by RPHPLC (40–60% C. over 30 min) to yield the title compound (19 mg) as a white lyophile: Tr=8.7 min (40–60% C. over 30 min); $^1$HNMR (d$_6$-Acetone, 300 MHz) δ 10.98 (s, 1H), 9.02 (s, 1H), 8.76 (s, 1H), 7.85 (d, 1H, J=8.8), 7.5 (m, 15H), 5.68 (d, 1H, J=7.6), 5.02 (m, 1H), 4.65 (ABq, 2H, J=16.8, 135), 4.02 (s, 3H), 2.19 (d, 3H, J=2.0), 2.18 (d, 3H, J=2.0); low resolution MS(FAB) m/e 617 (MH+).

Example 8

2-[2,4-dioxo-3-(3-phenyl-ureido)-5-pyridin-3-yl-2,3,4,5-tetrahydrobenzo[b][1,4]diazepin-1-yl]-N-isopropyl-N-(4-methoxy-phenyl) acetamide A solution of phenyl isocyanate (36.6 mg, 0.295 mmol) in methylene chloride (1 ml) was added to a solution of 2-(3-Amino-2,4-dioxo-5-pyridin-3-yl-2,3,4,5-tetrahydrobenzo[b][1,4]diazepin-1-yl)-N-isopropyl-N-(4-methoxy-phenyl) acetamide (140 mg, 0.295 mmol) in methylene chloride (1 ml) and the resultant solution stirred at rt for 16 h. The solvent was removed in vacuo and the residue recrystalised from 5% methanol in ethyl acetate to afford the title compound product (49 mg) as a white powder. 1H NMR (300 MHz, CDCl-3). s 8.72 (s, 1H), 8.56 (d, 1H, J=8.0), 7.92 (d, 1H, J=8.0), 6.91–7.43 (m, 16H), 6.43 (d, 1H, J=8.3), 5.43 (d, 1H, J=8.3), 4.95 (sept, 1H, J=6.8), 4.60 (d, 1H, J=11.8), 4.18 (d, 1H, J=11.8), 3.88 (s, 3H), 1.06 (m, 6H). Low resolution MS (FAB) m/e 593 (m+).

Example 9

3-(3-{1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid tert butyl ester Triphosgene (22.1 mg) was added to a 0° C. solution of t-butyl m-aminobenzoate (43.3 mg, 0.224 mmol) in THF (5 ml) and triethylamine (0.068 ml) and the resultant mixture stirred at 0° C. for 1 h prior to the addition of 2-(3-Amino-2,4-dioxo-5-pyridin-3-yl-2,3,4,5-tetrahydrobenzo[b][1,4]diazepin-1-yl)-N-isopropyl-N-(4-methoxy-phenyl) acetamide (106 mg, 0.224 mmol) and the resultant mixture stirred at rt overnight. The solvent was removed in vacuo and the residue dissolved in ethyl acetate (50 ml) and washed with 0.5N hydrochloric acid (2×30 ml), water (30 ml), brine (30 ml), dried (MgSO4) and concentrated in vacuo to afford the title compound (115 mg) as a white solid. 1H NMR (300 MHz, CDCl-3). s 8.62 (s, 1H), 8.59 (d, 1H, J=8.0), 7.92 (d, 1H, J=8.0), 6.91–7.83 (m, 15H), 6.43 (d, 1H, J=8.1), 5.43 (d, 1H, J=8.1), 4.91 (sept, 1H, J=6.8), 4.60 (d, 1H, J=11.8), 4.18 (d, 1H, J=11.8), 3.86 (s, 3H), 1.66 (s, 9H), 1.06 (m, 6H).

Example 10

3-(3-{1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid A mixture of 3-(3-{1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid tert butyl ester (115 mg, 0.224 mmol) and 4N HCl in dioxane (1 ml) was stirred at rt for 1.75 h after which time a further 1 ml of 4N HCl in dioxane was added and the reaction mixture stirred at rt overnight. Ether (20 ml) was added and the resultant precipitate was triturated with ether (3×30 ml) to afford the title compound as a white powder. 1H NMR (300 MHz, CDCl3).s 1H NMR (300 MHz, CDCl-3). s 8.61 (s, 1H), 8.56 (d, 1H, J=8.2), 7.91 (d, 1H, J=8.2), 6.91–7.83 (m, 16H), 6.41 (d, 1H, J=7.9), 5.43 (d, 1H, J=7.9), 4.91 (sept, 1H, J=6.8), 4.60 (d, 1H, J=11.8), 4.18 (d, 1H, J=11.8), 3.86 (s, 3H), 1.06 (m, 6H). Low resolution MS (FAB) m/e 637 (m+).

Example 11

1H-Indole-2-carboxylic acid {1-[Isopropyl-(4-methoxy-phenyl)-carbamoylmethyl]-2,4-indole dioxo-5-pyridin4-yl-2,3,4,5,5a, 9a-hexahydro-1H-benzo[b][1,4]diazepin-3-yl}-amide To a solution of 23.3 mg (0.049 mmol) 2-(3-Amino-2,4-dioxo-5-pyridin-4-yl-2,3,4,5,5a,9a-hexahydro-benzo[b][1,4]diazepin-1-yl)-N-isopropyl-N-(4-methoxyphenyl)-acetamide in 0.5 mL DMF were added 8.5 mg (0.052 mmol; 1.05 equiv) indole-2-carboxylic acid, 6.7 mg (0.049 mmol; 1 equiv) N-hydroxybenzotriazole, and 10.4 mg (0.054 mmol; 1.1 equiv) 1-(3-dimethylaminopropyl)-3-ethylcarbodiimide hydrochloride successively with stirring at ambient temperature. The resultant mixture was stirred at ambient temperature for 18 hours. The solvent was evaporated under reduced pressure to give a yellow oil which was taken into DCM (30 mL), washed with satd. NaHCO3, dried over MgSO4, filtered and concentrated under reduced pressure to a give a tan foam. The crude product was purified by flash chromatography on silica gel (4 g) eluted successively with ethyl acetate/hexanes (4:1; 100 mL), ethyl acetate (100 mL). Appropriate fractions were combined and concentrated in vacuo to give 10.2 mg (0.017 mmol) of the title compound as a white foam: 1H NMR (Acetone-d6, 300 MHz) d 10.83 (s, 1H), 8.63 (s, 1H), 7.69 (m, 2H), 7.61 (d, 1H, J=8.2), 7.53 (m, 3H), 7.45 (m, 1H), 7.38–7.28 (m, 4H), 7.23 (t, 1H), 7.09 (m, 4H), 5.50 (d, 1H, J=7.6), 4.85 (m, 1H), 4.65 (d, 1H, J=16.6), 4.28 (d, 1H, J=16.7), 3.86 (s, 3H), 1.01 (m, 6H); TLC Rf=0.36 (EtOAc); MS (FAB) m/z 617.3 (MH+).

Example 12

3-(3-{7-Fluoro-1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid tert butyl ester A solution of 84 mg of 2-(3-amino-7-fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide (0.165 mmol) in 4 mL of acetonitrile was combined with 59 mg of 3-[(4-nitrophenyl)oxycarbonyl]-amino-benzoic acid tert-butyl ester (0.165 mmol, 1 eq) and heated at reflux under nitrogen for 3 hrs. The resulting slurry was cooled to 5° C., held for 30 mins., filtered and dried under high vacuum to provide 93 mg of the title compound as a crystalline solid. 1H NMR (300 MHz, d6-DMSO) d 9.41 (s, 1H), 8.74 (d, 1H, J=2.3), 8.61 (dd, 1H, J=1.5, 4.9), 7.99 (m, 1H), 7.95 (m, 1H), 7.67 (dd, 1H, J=5.6, 9.3), 7.57 (m, 2H), 7.48 (m, 1H), 7.31 (m, 4H), 7.10 (d, 2H, J=8.9), 6.97 (d, 1H, J=7.7), 6.87 (dd, 1H, J=8.9), 5.16 (, 1H, J=7.6), 4.78 (m, 1H), 4.56 (d, 1H, J =16.5), 4.19 (d, 1H, J=16.5), 3.84 (s, 3H), 1.54 (s, 9H), 0.98 (m, 6H); low resolution MS (FAB)m/e 710 (MH+).

Example 13

3-(3-{7-Fluoro-1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid A mixture of 84 mg of 3-(3-{7-fluoro-1-[isopropyl-(4-methoxy-phenyl)-carbamoylmethyl]-2,4-dioxo-5-pyridin-3-yl-2,3,4,5-tetrahydro-1H-benzo[b][1,4]diazepin-3-yl}-ureido)-benzoic acid tert butyl ester (0.118 mmol) and 4 mL of trifluoroacetic acid was stirred under nitrogen for 1.5 hrs. The trifluoroacetic acid was removed in vacuo and the residue was triturated with diethyl ether. The slurry was filtered, washed with diethyl ether and dried under high vacuum to provide 85 mg the title compound as a white crystalline trifluoroacetic acid salt. 1H NMR (300 MHz, d6-DMSO) d 9.33 (s, 1H), 8.70 (b, 1H), 8.57 (d, 1H, J=4.7), 8.00 (m, 1H), 7.97 (d, 1H, J=8.6), 7.61 (dd, 1H, J=5.5, 9.1), 7.55 (dd, 1H, J=4.88, 8.2), 7.47 (m, 2H), 7.26 (m, 4H), 7.05 (d, 2H, J=9.0), 6.92 (d, 1H, J=7.8) 6.82 (dd, 1H, J=2.8, 9.6), 5.10 (d, 1H, J=7.6), 4.72 (m, 1H), 4.51 (d, 1H, J=16.8), 4.14 (d, 1H, J=16.8), 3.78 (s, 3H), 0.92 (m, 6H); low resolution MS (FAB)m/e 655 (MH+).

Examples 14 and 15

(+) or (−) 1H-Indole-2-carboxylic acid [1-[isopropyl-(4-methoxyphenyl)-carbamoylmethyl]-2,4-dioxo-5-pyridin-3-yl-2,3,4,5-tetrahydro-1H-benzo[b][1,4]diazepin-3-yl]amide Enantiomers of Example 7 were separated (>99.9% ee) by preparative high pressure liquid chromatography (HPLC) using a waters Model 4000 Delta Prep equipped with a Daicel Chemical Industries Chiralpak-AD preparative column (20 micron,5 cm×50 cm) as the stationary phase. The mobile phase employed was 72% hexane/21% isopropyl alcohol/7% chloroform. Isocratic conditions were used with a flow rate of 50 mL/min (to=16 min).Appropriate fractions were combined, concentrated in vacuo, and lyophilized from water and acetonitrile to obtain the target analogs. Analytical purity was assessed by HPLC using a Hewlett Packard 1050 system equipped with a Hewlett Packard 1050 diode array spectrometer (lambda range 200–400). The stationary phase was a Daicel Chemical Industries Chiralpak-AD (10 micron, 0.46 cm×25 cm). The mobile phases were the same as above and the flow rate was 1.0 mL/min (to=3 min). The retention time, tR, in minutes for the two isomers were as follows.

Enantiomer 1 Example 14: tR=25.06 min.

Enantiomer 2, Example 15: tR=81.39 min.

Intermediate 1

Isopropyl-(4-methoxyphenyl)amine

To a stirred solution of 4-methoxyphenylamine (1.24 g, 6.22 mmol) in methanol (15 mL) at ambient temperature was added successively, glacial acetic acid (415 mg, 6.91 mmol), acetone (669 mg, 11.5 mmol), and 1M sodium cyanoborohydride in THF (12.7 mL, 12.6 mmol). The reaction mixture was stirred overnight at room temperature. The pH was adjusted to 2 with 6N HCl and stirred for 30 minutes to quench excess sodium cyanoborohydride. The pH was then adjusted to 8.5 with 1N NaOH and the resultant solution extracted with diethyl ether (2×50 mL) and ethyl acetate (50 mL). The organic extracts were combined, dried over sodium sulfate, filtered and concentrated under reduced pressure to give the title compound (1.42 g, 5.91 mmol) as a yellow oil. $^1$H NMR (300 MHz, CDCl$_3$): δ 6.78(d, J=8.8 Hz, 2H), 6.57(d, J=9.1 Hz, 2H), 3.75(s, 3H), 3.55(m, 1H), 2.92(br s, 1H), 1.18(d, J=6.1 Hz, 6H); TLC (EtOAc/Hex (2:3)): R$_f$=0.72

Intermediate 2

2-Bromo-N-isopropyl-N-(4-methoxyphenyl)acetamide

To a solution of isopropyl-(4-methoxyphenyl)-amine (25.11 g, 152 mmol) in dichloromethane (250 mL) was added triethylamine (15.38 g, 152 mmol) with stirring at ambient temperature. The solution was cooled in an ice bath (<3° C.) and bromoacetyl bromide (30.68 g, 152 mmol) dissolved in dichloromethane (100 mL) was added dropwise over a 45 minute period. The reaction mixture was stirred overnight at ambient temperature, washed with 0.3N HCl (300 mL) and brine (300 mL), dried over sodium sulfate, filtered, and evaporated under reduced pressure to give a dark brown oil. The oil was filtered through a pad of silica gel (150 g) which was eluted with ethyl acetate/hexane (1:1, 900 mL) and the filtrate evaporated under reduced pressure to afford the title compound (41.05 g, 143 mmol) as a brown oil which crystallized on standing.

$^1$H NMR (300 MHz, CDCl$_3$): d 1.04(d, J=6.8 Hz, 6H), 3.53(s, 2H), 3.84(s, 3H), 4.93(m, 1H), 6.93(d, J=9.1 Hz, 2H), 7.10(d, J=9.1 Hz, 3H) TLC (EtOAc/Hexane(3:17)): R$_f$=0.18

Intermediate 3

2-(phenylhydrazono)-malonic acid

To a vigorously stirred solution of ketomalonic acid monohydrate (29.33 g) in ethanol (140 mL) and water (300 mL) at ambient temperature was added phenylhydrazine (23.3 g) dropwise over a 40 minute period. The resultant slurry was stirred overnight at ambient temperature. The solid was separated by filtration, washed sucessively with cold water (100 mL) and ethanol (25 mL) and air dried. Subsequent drying was performed at 75° C. overnight in a vacuum oven to give the title compound as a yellow solid (42.38 g). $^1$H (300 MHz, DMSO-d$_6$): d 7.12(t, 1H), 7.35–7.48(m, 4H); m.p.: 155°–157° C. (dec).

Intermediate 4

2-(phenylhydrazono)-propanedioyl dichloride

To a stirred slurry of 2-(phenylhydrazono)-malonic acid (14.73 g), in chloroform (90 mL) at 5° C. was added phosphorous pentachloride (36.84 g) portionwise over a 20 minute period. After complete addition, the solution was warmed to room temperature and stirred one hour, then heated to reflux for three hours. The solution was cooled in an ice bath and the resultant precipitate was separated by filtration, washed with cold hexane (50 mL), and dried under vacuum overnight to give the title compound (13.4 g) as a bright yellow solid. $^1$H (300 MHz, DMSO-d$_6$): d 7.12(t, 1H), 7.20–7.56(m, 4H); m.p.: 135°–138° C. (dec).

Intermediate 5

2-(2-Aminopyridyl)nitrobenzene

Sodium hydride (60% in oil, 1.26 g) was added to a 0° C. solution of 2-aminopyridine (2.00 g) in THF (10 ml) and the resultant mixture stirred at 0° C. for 1 h. A solution of 2-fluoronitrobenzene (2.21 ml) in THF (8 ml) was added dropwise and the resultant mixture allowed to attain rt overnight. Saturated aqueous sodium carbonate (10 ml) was added and the separated aqueous phase extracted into dichloromethane (3×10 ml). The combined organic extracts were washed with brine (20 ml), dried (MgSO$_4$) and concentrated in vacuo. Flash column chromatography (cyclohexane: ethyl acetate; 3:1 as eluant) gave the title compound (2.23 g) as an orange/red solid.

$^1$H NMR (300 MHz, CDCl$_3$); 6.83 (m, 3H), 7.42 (dr, J=1,7 Hz, 1H), 7.40 (dr, J=1.7 Hz, 1H), 8.08 (dd, J=1.7 Hz, 1H), 8.21 (d, J=1,1.5 Hz, 1H), 8.61 (dr, J=1.7 Hz, 1H), 10.0 (s, 1H). Mp=71° C.

Intermediate 6

N-(2-pyridyl)phenylene diamine 2-(2-Aminopyridyl)nitrobenzene (2.14 g)was dissolved in glacial acetic acid (45 ml) and iron filings (5.57 g) were added and the resultant mixture stirred at rt for 72 h after which time the solids were removed by filtration through celite and the solvent removed by concentration in vacuo. Aqueous sodium carbonate (2M) solution was added adjust the pH of the solution to pH 8 and this mixture was then extracted into dichloromethane (3×30 ml). The combined organics were washed with brine (30 ml), dried (MgSO$_4$) and concentrated in vacuo to afford the title compound (1.68 g) as a beige solid. $^1$H NMR (300 MHz, CDCl$_3$); 6.12 (br, 2H), 6.42 (d, J=6 Hz, 1H), 6.68 (m, 1H), 6.78 (m, 3H), 7.008 (dt, J=1, 6.0 Hz, 1H), 7.15 (dd, J=1.5,8 Hz, 1H), 7.42 (m, 1H), 8.15 (br, 1H).Tlc (cyclohexane:ethyl acetate; 1:1)Rf= 0.2

Intermediate 7

N-Isopropyl-N-(4-methoxy-phenyl)-2-[2-(pyridin-2-ylaminophenylamino]-acetamide A mixture of N-(2-pyridyl)phenylene diamine (2.00 g), isopropyl-(4-methoxyphenyl)amine (3.08 g) and potassium carbonate (1.50 g) in DMF (30 ml) was stirred at rt for 22 h. The solvents were removed in vacuo and the residue was partitioned between ethyl acetate (50 ml) and water (3×30 ml). The organic phase was washed with brine (30 ml), dried (MgSO$_4$) and concentrated in vacuo to afford the crude title product as a brown solid. Two recrystalizations from ethyl acetate:hexane (1:1) gave the title compound as a fawn solid. $^1$H NMR (300 MHz, CDCl$_3$); 1.01 (d, J=7 Hz, 6H), 3.4 (s, 2H), 3.83 (s, 3H), 4.98 (sept, J=7 Hz), 6.08 (s 1H), 6.31 (d, J=8.5 Hz, 1H), 6.42 (d, J=8.0 Hz, 1H), 6.66 (m, 2H), 6.9–7.1 (m, 6H), 7.22 (d, J=8.0 Hz 1H), 7.40 (t, J=6.5 Hz, 1H), 8.18 (d, J=3.5 Hz, 1H). Tlc (10% MeOH, CH$_2$Cl$_2$) Rf=0.42.

Intermediate 8

2-[2,4-Dioxo-3(phenyl-hydrazono)-5-pyridin-2-yl-2,3,4,5-tetrahydrobenzo[b][1,4]diazepin-1-yl]-N-isopropyl-N-(4-methoxyphenyl)-acetamide A solution of N-Isopropyl-N-(4-methoxyphenyl)-2-[2-(pyridin-2-ylaminophenylamino]]-acetamide (500 mg) in THF (20 ml) and 2-(phenylhydrazono)propanedioyl dichloride (317 mg) in THF (20 ml) was added concurrently to a 0° C. sample of THF (20 ml) and the resultant mixture was allowed to warm to rt overnight. The solvents were removed in vacuo and the residue was dissolved in ethyl acetate (50 ml) and washed with 2N aqueous sodium bicarbonate (2×30 ml), water, (30 ml), brine (30 ml), dried (MgSO$_4$) and concentrated in vacuo to afford the crude product. Flash column chromatography on silica gel, eluting with 10% methanol/methylene chloride, gave the title compound as a 3:2 mixture of hydrazones (460 mg). Due to the mixture of diastereomers, the $^1$H NMR data were not diagnostic. Tlc (10% MeOH, CH$_2$Cl$_2$) Rf=0.62.

Intermediate 9

2-(3-Amino-2,4-dioxo-5-pyridin-2-yl-2,3,4,5-tetrahydro-benzo[b][1,4]diazepin-1-yl)-N-isopropyl-N-(4-methoxy-phenyl)-acetamide A mixture of 2-[2,4-Dioxo-3(phenyl-hydrazono)-5-pyrdin-2-yl-2,3,4,5-tetrahydrobenzo[b][1,4]diazepin-1-yl]-N-isopropyl-N-(4-methoxy-phenyl)-acetamide (460 mg), zinc dust (430 mg) and acetic acid (5.6 ml) was stirred at rt for 3 h. The solids were removed by filtration through celite, the filtrate was concentrated in vacuo and the residue azeotroped with hexane. The residue was dissolved in ethyl acetate (50 ml) and washed with 2N aqueous sodium bicarbonate (2×30 ml), water, (30 ml), brine (30 ml), dried (MgSO$_4$) and concentrated in vacuo to afford the crude product (270 mg) which was used without further purification. $^1$H NMR (300 MHz, CDCl$_3$); 1.03 (d, J=7 Hz, 6H), 3.79 (s, 3H), 4.02 (d J=10 Hz, 1H), 4.40 (s, 1H), 4.42 (d, J=10 Hz, 1H), 5.0 (sept, J=7.1 Hz, 1H), 6.8–7.3 (m, 10H), 7.44 (d, J=8.0 Hz 1H), 7.68 (d, J=8.0 Hz, 1H), 7.80 (m, 1H), 8.42 (d, J=3.9 Hz, 1H). Tlc (10% MeOH, CH$_2$Cl$_2$) Rf=0.23.

Intermediate 10

(2-Nitro-phenyl)-pyrimidin-2-yl-amine

To a solution of 2-aminopyrimidine (10 g, 105 mmol) in DMF (100 mL) cooled to 5° C. was added 60% sodium hydride in mineral oil (5.47 g, 137 mmol) and the resulting mixture was stirred one hour with cooling. 1-fluoro-2-nitrobenzene (14.83 g, 105 mmol) in DMF (30 mL) was added dropwise over a 20 minute period to the cooled, stirring solution. The solution was allowed to warm slowly to ambient temperature and stirred 3 h. The product was precipitated with the addition of water (300 mL), separated by filtration, and dried to give the title compound (13.39 g, 61.9 mmol) as an orange solid: $^1$H NMR (Acetone-d$_6$, 400 MHz): 10.34 (br s, 1H), 9.00 (d, 1H, J=8.6 Hz), 8.60 (d, 2H, J=4.8 Hz), 8.23 (d, 1H, J=8.4 Hz), 7.74 (t, 1H), 7.17 (t, 1H), 7.06 (t, 1H); TLC (EtOAc/Hexanes (3:17)): R$_f$=0.27.

Intermediate 11

N-Pyrimidin-2-yl-benzene-1,2-diamine

To a solution of (2-nitrophenyl)-pyrimidin-2-yl-amine (13.2 g, 61.1 mmol) in a mixture of EtOAc (450 mL) and CH$_3$OH (350 mL) was added Raney Nickle (16 g (water wet)) and the reaction mixture hydrogenated under 1 atm hydrogen at ambient temperature for 3 h. The catalyst was separated by filtration and the filtrate concentrated in vacuo to a red-brown solid which upon trituration with cold CH$_3$OH (250 mL) gave the title compound (8.21 g, 44.1 mmol) as a grey solid: $^1$H NMR (CDCl$_3$, 400 MHz): 8.38 (d, 2H, J=4.9 Hz), 7.37 (d, 1H, J=7.9 Hz), 7.08 (t, 1H), 7.00 (br s, 1H), 6.83 (m, 2H), 6.67 (t, 1H), 3.60 (br s, 2H); TLC (EtOAc/Hexanes(2:1)): R$_f$=0.33.

Intermediate 12

N-Isopropyl-N-(4-methoxy-phenyl)-2-[2-(pyrimidin-2-ylamino)-phenylamino]-acetamide To a solution of N-pyrimidin-2-yl-benzene-1,2-diamine (82 mg, 0.441 mmol) in DMF (2 mL) was added potassium carbonate (61 mg, 0.441 mmol), potassium iodide (7 mg, 0.044 mmol), and 2-Bromo-N-isopropyl-N-(4-methoxy-phenyl)-acetamide (126 mg, 0.441 mmol). The resultant reaction mixture was stirred overnight at 60° C. The solvent was removed in vacuo and the crude material partitioned between CH$_2$Cl$_2$ (35 mL) and water (15 mL). The organic phase was separated, dried with MgSO$_4$, filtered and concentrated to a yellow oil which upon trituration with EtOH (6 mL) and filtration gave the title compound (96.7 mg, 0.247 mmol) as yellow crystals: $^1$H NMR (CDCl$_3$, 300 MHz): 8.36 (d, 2H, J=4.9 Hz), 7.38 (dd, 1H, J=1.2, 7.8 Hz), 7.06–6.90 (m, 6H), 6.75 (t, 1H), 6.66 (t, 1H), 6.36 (dd, 1H, J=1.2, 7.8 Hz), 4.97 (m, 1H), 3.87 (s, 3H), 3.43 (s, 2H), 1.04 (d, 6H, J=6.8 Hz); TLC (EtOAc): R$_f$=0.62; MS (FAB) m/z 392.0 (MH$^+$).

Intermediate 13

2-[2,4-dioxo-3-(phenyl-hydrazono)-5-pyrimidin-2-yl-2,3,4,5-tetrahydrobenzo[b][1,4]diazepine-1-yl]-N-isopropyl-N-4-methoxy-phenyl)-acetamide To a slurry of N-isopropyl-N-(4-methoxy-phenyl)-2-[2-(pyrimidin-2-ylamino)phenylamino]-acetamide (500 mg, 1.28 mmol) in THF (12 mL) cooled in an ice bath was added of 2-(phenyl-hydrazono) propandioyl dichloride (344 mg, 0.141 mmol) in THF (6 mL) dropwise over 5 minutes. After complete addition, the solution was allowed to warm to room temperature and stirred overnight. The solvent was evaporated under reduced pressure and the resultant oil dissolved in ethyl acetate (80 mL), washed with saturated sodium bicarbonate solution, dried over MgSO$_4$, filtered and concentrated under reduced pressure to give a yellow oil. The crude product was purified by flash chromatography on silica gel (15 g) eluting with EtOAc/Hexanes (2:1, 250 mL). Appropriate fractions were combined and concentrated to give the title compound (500 mg, 0.886 mmol) as a yellow foam: $^1$H NMR (CDCl$_3$, 300 MHz): 11.22 (s, 1H), 8.58 (m, 2H), 7.70–6.90 (m, 14H), 5.05 (m, 1H), 4.46 (m, 1H), 3.82 (m, 4H), 1.12 (m, 6H); TLC (EtOAc/Hexanes(2:1)): R$_f$=0.21; MS (FAB) m/z 564.1 (MH$^+$).

Intermediate 14

2-(3-Amino-2,4-dioxo-5-pyrimidin-2-yl-2, 3, 4, 5-tetrahydro-benzo[b][1,4]diazepine-1-yl)-N-isopropyl-N-(4-methoxy-phenyl)-acetamide To a stirred solution of 2-[2,4-dioxo-3-(phenyl-hydrazono)-5-pyrimidin-2-yl-2,3,4,5-tetrahydro-benzo[b][1,4]diazepine-1-yl]-N-isopropyl-N-(4-methoxy-phenyl)-acetamide (500 mg, 0.886 mmol) in acetic acid (12 mL) at ambient temperature was added zinc dust (530 mg) and the resulting mixture was stirred 1 h. The zinc was separated by filtration, the filtrate concentrated in vacuo, and the resultant oil partitioned between water (30 mL) and ethyl acetate (80 mL). The pH was adjusted to 8 with 6N sodium hydroxide and the phases were separated. The aqueous phase was extracted with ethyl acetate (2×35 mL) and the organics combined, dried with magnesium sulfate, filtered and concentrated in vacuo to give a yellow foam. The crude product was purified via flash chromatography on silica gel (15 g) eluting with methylene chloride/methanol (19:1, 250 ml). Appropriate fractions were combined and concentrated to give the title compound (255 mg, 0.537 mmol) as a white glass:

$^1$H NMR (CDCl$_3$, 400 MHz): 8.78 (d, 2H, 4.9 Hz), 7.59 (dd, 1 h, J=1.1,8.3 Hz), 7.33 –7.25 (m, 3H), 7.16 (t, 1H), 7.05 (dd, 1H, J=1.4,8.3 Hz), 6.96 (dd, 1H, J=2.7,8.7 Hz), 6.89 (dd, 1H, J=2.7, 8.5 Hz), 6.86 (dd, 1H, J=1.2,8.2 Hz), 5.06 (m, 1H), 4.52 (d, 1H, J=16.6 Hz), 4.43 (s, 1H), 3.85 (d, 1H, J=16.6 Hz), 3.82 (s, 3H), 2.60 (br s, 2H), 1.11 (d, 6H, J=1.0 Hz); TLC (CH$_2$Cl$_2$/CH$_3$OH (9:1)): R$_f$=0.48; MS (FAB) m/z 475.3 (MH$^+$).

Intermediate 15

(2-Nitrophenyl)-(1,3,5-trimethyl-1H-pyrazol-4-yl)-amine

To a solution of 1-fluoro-2-nitrobenzene (7.47 mL, 70.9 mmol) in ethanol (35 mL) and H$_2$O (105 mL) was added 4-amino-1,3,5-trimethylpyrazole (8.8 g, 70.9 mmol). The solution was refluxed for 15 h, then cooled to room temperature. The precipate was separated by filteration and washed with 25% aqueous ethanol to yield the title compound (8.6 g): $^1$HNMR (CDCl$_3$, 300 MHz) δ 8.81 (s, 1H), 8.18 (dd, 2H, J=1.6, 8.7), 6.69(m, 1H) 6.61 (dd, 1H, J=1.2, 8.7), 3.77 (s, 3H), 2.10 (s, 3H), 2.06 (s, 3H); low resolution MS(FAB) m/z 247(MH$^+$).

Intermediate 16

N-(1,3,5-Trimethyl-1H-pyrazol-4-yl)-benzene-1,2-diamine

To a solution of (2-Nitro-phenyl)-(1,3,5-trimethyl-1H-pyrazol-4-yl)-amine (8.6 g, 35 mmol) in ethyl acetate (175 mL) was added 10% palladium on carbon (1 g). The solution was stirred under a hydrogen atmosphere (50 psi) for 15 h and subsequently filtered through a bed of celite, washed with ethyl acetate, and concentrated in vacuo to yield the title compound (7.56 g): $^1$HNMR (CDCl$_3$, 300 MHz) δ 6.74 (m, 3H), 6.32 (d, 1H, J=1.9, 7.2), 4.6 (s, 1H), 3.75 (s, 3H), 3.1 (s, 2H), 2.05 (m, 6H); low resolution MS(FAB) m/z 217 (MH$^+$).

Intermediate 17

N-Isopropyl-N-(4-methoxy-phenyl)-2-[2-(1,3,5-trimethyl-1H-pyrazol-ylamino)-phenylamino]-acetamide To a solution of N-(1,3,5-Trimethyl-1H-pyrazol-4-yl)-benzene-1,2-diamine (7.56 g, 35.0 mmol) and 2-bromo-N-isopropyl-N-(4-methoxy-phenyl)-acetamide (7.18 g, 38.5 mmol) in DMF (70 mL) was added potassium carbonate (14.5 g, 105 mmol) and potassium iodide (581 mg, 3.5 mmol). The solution was heated at 80° C. for 15 h and subsequently poured into DCM (100 mL). The mixture was extracted with $H_2O$ (×4), 1N HCl (×2) and brine, dried over $MgSO_4$ and concentrated in vacuo. The resulting foam was purified by trituration with $Et_2O$ to yield the title compound (11.9 g):

$^1$HNMR (CDCl$_3$, 300 MHz) δ 8.08 (s, 1H), 7.07 (dd, 4H, J=2.2, 6.6), 6.63 (m, 2H), 6.31 (m, 2H), 5.03 (m, 1H), 4.76 (s, 1H), 3.87 (s, 3H), 3.74 (s, 3H), 3.46 (s, 2H), 2.02 (m, 6H), 1.07 (d, 6H, J=6.8); low resolution MS(FAB) m/z 422 (MH$^+$).

Intermediate 18

2-[2,4-Dioxo-3-(phenyl-hydrazono)-5-(1,3,5-trimethyl-1H-pyrazol-4-yl)-2,3,4,5-tetrahydro-benzo[b][1,4]diazepin-1-yl]-N-isopropyl-N-(4-methoxy-phenyl)-acetamide A solution of N-Isopropyl-N-(4-methoxy-phenyl)-2-[2-(1,3,5-trimethyl-1H-pyrazol-ylamino)-phenylamino]-acetamide (3.0 g, 7.1 mmol) in THF (70 mL) and a solution of 2-(phenyl-hydrazono)-propanedioyl dichloride (1.75 g, 7.1 mmol) in THF (70 mL) were simultaneously added to THF (35 mL) cooled to 0° C. The solution stirred at RT for 15 h and was subsequently concentrated in vacuo to yield the title compound (8.1 g) which was used without further purification.

Intermediate 19

2-[3-Amino-2,4-dioxo-5-(1,3,5-trimethyl-1H-pyrazol-4-yl)-2,3,4,5-tetrahydro-benzo[b][1,4]diazepin-1-yl]-N-isopropyl-N-(4-methoxy-phenyl)-acetamide To a solution of 2-[2,4-Dioxo-3-(phenyl-hydrazono)-5-(1,3,5-trimethyl-1H-pyrazol-4-yl)-2,3,4,5-tetrahydro-benzo[b][1,4]diazepin-1-yl]-N-isopropyl-N-(4-methoxy-phenyl)-acetamide (4.6 g, 7.74 mmol) in glacial acetic acid (45 mL) was added zinc dust (4.6 g). The heterogenous solution stirred at RT for 15 h and subsequently filtered through a bed of celite, washed with ethyl acetate and concentrated to dryness. The resulting oil was dissolved in ethyl acetate (200 mL) and extracted with saturated sodium bicarbonate (×3), brine, dried $MgSO_4$, and concentrated in vacuo. The resulting oil was purified by silica gel flash chromatography (5% methanol/DCM) to yield the title compound (385 mg): $^1$HNMR (CDCl$_3$, 300 MHz) δ 7.60–6.80 (m, 10H), 5.05 (m, 1H), 4.4(m, 1H), 3.82 (s, 3H), 3.74 (s, 3H), 3.62 (s, 2H), 2.24 (s, 3H), 1.20 (s, 3H), 1.09 (m, 6H); low resolution MS(FAB) m/z 505 (MH$^+$).

Intermediate 20

4-methoxybenzyl)-(2-nitrophenyl)-amine

To 2-fluronitrobenzene (80.65 mL, 0.77 mmol) dissoved in ethanol (200 mL and water (600 mL) was added 4-methoxybenzylamine (100 mL, 0.77 mmol). The reaction mixture was heated at 92_C. for 15 h, cooled to room temperature, and the orange precipitate was separated by filtration. The precipitate was recrystalized from ethanol:water 1/3, then dissolved in ethyl acetate, dried over $MgSO_4$, and concentrated in vacuo to yield the title compound (117.88 g): $^1$HNMR (300 MHz, CDCl$_3$) d 8.35 (bs, 1H), 8.18 (d, J=8.5 Hz, 1H), 7.38 (dd, J=7.3, 7.8 Hz, 1H) 7.27 (d, J=8.5 Hz, 2H), 6.85 (m, 3H), 6.66 (dd, J=7.3, 7.8 Hz, 1H), 4.47 (collapsed ABq, J=4.9 Hz, 2H), 3.81 (s, 3H); low resolution MS(FAB) m/z 258.99 (MH$^+$).

Intermediate 21

N-(4-methoxy-benzyl)-benzene-1,2-diamine

Zinc dust (50 g) was added to 4-methoxybenzyl)-(2-nitrophenyl)-amine (50 g, mmol) in glacial acetic acid (500 mL) cooled to 15_C. in a three-neck round bottom fitted with an overhead stirrer. The reaction mixture was warmed to room temperature and stirred 15 h. The reaction mixture was filtered through a pad of celite, and the filtrate was concentrated to dryness. The resulting oil was taken up in ethyl acetate/water and the pH of the aqueous layer was adjusted to 8 with sodium bicarbonate. The aqueous layer was extracted with ethyl acetate (×4), dried over $MgSO_4$ and concentrated in vacuo. The crude product was purified by silica gel flash chromatography (50% hexane/DCM) to yield the title compound (33.34 g):

$^1$HNMR (300 MHz, CDCl$_3$) d 7.32 (d, J=8.5 Hz, 2H), 6.88 (d, J=8.5 Hz, 2H), 6.97 (m, 4H), 4.25 (s, 2H), 3.81 (s, 3H); low resolution MS(FAB) m/z 476 (MH$^+$)

Intermediate 22

N-Isopropyl-2-[2-(4-methoxy-benzylamino)-phenylamino]-N-(4-methoxy-phenyl)-acetamide To a solution of N-(4-methoxybenzyl)-benzene-1,2-diamine (2.42 g, 10.6 mmol) in DMF (40 mL) was added potassium carbonate (1.47 g,10.6 mmol), potassium iodide (176 mg, 1.06 mmol), and 2-Bromo-N-isopropyl-N-(4-methoxy-phenyl)-acetamide acetamide (3.03 g, 10.6 mmol). The resultant reaction mixture was stirred overnight at 60° C. The solvent was removed in vacuo and the crude material dissoved in EtOAc (150 mL), washed with water (2×50 mL) and brine (50 mL), dried with $MgSO_4$, filtered and concentrated to a brown oil. The precipitate which formed upon the addition of ether (70 mL) was filtered to give the title compound (1.39 g, 3.21 mmol) as a yellow solid. The remaining filtrate was concentrated under reduced pressure to a brown oil which was purified by flash chromatography on silica gel (40 g) eluted with EtOAc/Hexanes (1:4, 900 mL).

Appropriate fractions were combined and concentrated under reduced pressure to give a second crop of the title compound (1.86 g, 4.29 mmol) as a brown oil:

$^1$H NMR (300 MHz, CDCl$_3$): d 7.30 (m, 2H), 7.05 (m, 2H), 6.95 (m, 2H), 6.88 (m, 2H), 6.73–6.61 (m, 3H), 6.28 (m, 1H), 5.01 (m, 1H), 4.23 (s, 2H), 3.87 (s, 3H), 3.80 (s, 3H), 3.40 (s, 2H), 1.07 (m, 6H); TLC (EtOAc/Hexanes (1:4)): R$_f$=0.14.

Intermediate 23

N-Isopropyl-2-[5-(4-methoxy-benzyl)-2,4-dioxo-3-(phenyl-hydrazono)-2,3,4,5-tetrahydro-benzo[b][1,4]diazepin-1-yl]-N-(4-methoxy-phenyl)-acetamide To a solution of N-isopropyl-2-[2-(4-methoxybenzylamino)-phenylamino]-N-(4-methoxy phenyl)-acetamide (3.25 g, 7.51 mmol) in THF (50 mL) cooled in an ice bath (<5° C.) was added 2-(phenyl-hydrazono) propandioyl dichloride (1.84 g, 7.51 mmol) in THF (50 mL) dropwise over 20 minutes. After complete addition, the solution was allowed to warm to room temperature and stirred overnight. The solvent was evaporated under reduced pressure and the resultant oil was dissolved in ethyl acetate (300 mL), washed with saturated sodium bicarbonate solution (100 mL) and brine (50 mL), dried over $MgSO_4$, filtered and concentrated under reduced pressure to give the title compound (4.55 g, 7.51 mmol) as a yellow oil: $^1$H NMR (300 MHz, CDCl$_3$): d 11.46 (s, 0.5H), 10.69 (s, 0.5H), 7.56–6.95 (m, 15H), 6.77–6.66 (m, 2H), 5.34 (m, 1H), 5.05 (m, 1H), 4.79 (m, 1H), 4.34–4.08 (m, 2H), 3.86 (s, 2H), 3.74 (s, 3H), 3.72 (s, 3H), 1.11 (m, 6H); TLC (EtOAc/Hexanes(2:3)): R$_f$=0.30.

Intermediate 24

2-[3-Amino-5-(4-methoxy-benzyl)-2,4-dioxo-2,3,4,5-tetrahydro-benzo[b][1,4]diazepin-1-yl]-N-isopropyl-N-(4-methoxy-phenyl)-acetamide To a stirred solution of N-Isopropyl-2-[5-(4-methoxybenzyl)-2,4-dioxo-3-(phenyl-hydrazono)-2,3,4,5-tetrahydro-benzo[b][1,4]diazepin-1-yl]-N-(4-methoxyphenyl)-acetamide (4.55 g, 7.51 mmol) in acetic acid (50 mL) was added zinc dust (4.50 g) and the resultant mixture was stirred 4 hours at ambient temperature. The zinc was separated by filtration, the filtrate was concentrated in vacuo, and the resultant oil partitioned between water (150 mL) and ethyl acetate (250 mL). The pH was adjusted to 8 with 6N sodium hydroxide and the phases separated. The aqueous phase was extracted with ethyl acetate (2×80 mL) and the organics combined, dried with magnesium sulfate, filtered and concentrated in vacuo to a brown oil. The crude product was purified via flash chromatography on silica gel (70 g) eluting successively with EtOAc/Hexanes (2:1, 500 mL) and methylene chloride/methanol (19:1, 500 mL). Appropriate fractions were combined and concentrated to give the title compound (2:85 g, 5.52 mmol) as a brown oil: $^1$H NMR (300 MHz, CDCl$_3$): d 7.43 (d, J=7.3 Hz, 1H), 7.30–7.19 (m, 4H), 7.05–6.90 (m, 5H), 6.59 (d, J=8.8 Hz, 2H), 5.13 (d, J=15.1 Hz, 1H), 5.00 (m, 1H), 4.86 (d, J=15.1 Hz, 1H), 4.25 (s, 1H), 4.21 (d, J=16.6 Hz, 1H), 3.85 (s, 3H), 3.69 (s, 3H), 3.48 (d, J=16.6 Hz, 1H), 1.09 (m, 6H); TLC (CH$_2$Cl$_2$/CH$_3$OH (29:1)): R$_f$=0.11.

Intermediate 25

2-(3-Amino-2,4-dioxo-2,3,4,5-tetrahydro-benzo[b][1,4]diazepin-1-yl)-N-isopropyl-N-(4-methoxyphenyl)-acetamide To a stirred solution of 2-[3-Amino-5-(4-methoxybenzyl)-2,4-dioxo-2,3,4,5-tetrahydro-benzo[b][1,4]diazepin-1-yl]-N-isopropyl-N-(4-methoxyphenyl)-acetamide (2.63 g, 5.09 mmol) in acetonitrile/H$_2$O (9:1, 70 mL) at ambient temperature was added cerric ammonium nitrate (10.05 g, 18.3 mmol) portionwise over one hour. The solution was stirred overnight at room temperature. The solution was concentrated in vacuo, chased with toluene (2×50 mL) and the residue was extracted with CH$_2$Cl$_2$ (3×50 mL), filtered and concentrated to an orange glass. The crude product was purified by flash chromatography on silica gel (100 g) eluting successively with CH$_2$Cl$_2$/CH$_3$OH (15:1, 1.5 L) and CH$_2$Cl$_2$/CH$_3$OH (10:1, 1.3 L). Appropriate fractions were combined and concentrated under reduced pressure to give the title compound (1.97 g, 4.97 mmol) as a brown foam: $^1$H NMR (300 MHz, DMSO-d6): d 10.68 (br s, 1H), 7.39–6.98 (m, 8H), 5.75 (s, 1H), 4.76 (m, 1H), 4.16–3.92 (m, 4H), 3.7 (s, 3H), 3.15 (m, 2H), 0.97 (m, 6H); TLC (CH$_2$Cl$_2$/CH$_3$OH (13:1)): R$_f$=0.21.

Intermediate 26

1H-Indole-2-carboxylic acid {1-[isopropyl-(4-methoxyphenyl)-carbamoylmethyl]-2,4-dioxo-2,3,4,5-tetrahydro-1H-benzo[b][1,4]diazepin-3-yl}-amide To a solution of 2-(3-Amino-2,4-dioxo-2,3,4,5-tetrahydro-benzo[b][1,4]-diazepin-1-yl)-N-isopropyl-N-(4-methoxyphenyl)-acetamide (350 mg, 0.883 mmol) in DMF (10 mL) were added indole-2-carboxylic acid (142 mg, 0.883 mmol), N-hydroxybenzotriazole (119 mg, 0.883 mmol), and 1-(3-dimethylaminopropyl)-3-ethylcarbodiimide hydrochloride (169 mg, 0.883 mmol) successively with stirring. The resultant mixture was stirred at ambient temperature for 18 hours. The solvent was evaporated under reduced pressure to give a yellow oil which was dissolved in ethyl acetate (60 mL), washed with water (20 mL) and brine (20 mL), dried over MgSO$_4$, filtered and concentrated under reduced pressure to a yellow oil which solidified on standing. The crude product was triturated with boiling ethanol (20 mL), cooled, filtered, and dried to give the title compound (169 mg, 0.313 mmol) as a yellow solid: $^1$H NMR (300 MHz, Acetone-d$_6$): d 10.85 (br s, 1H), 9.83 (brs, 1H), 7.67 (m, 2H), 7.53 (m, 2H), 7.37–7.20 (m, 7H), 7.04 (m, 3H), 5.28 (d, J=7.5 Hz, 1H), 4.87 (m, 1H), 4.31 (d, J=16.3 Hz, 1H), 4.13 (d, J=16.6 Hz, 1H), 3.83 (s, 3H), 1.02 (m, 6H); TLC (CH$_2$Cl$_2$/CH$_3$OH (19:1)): R$_f$=0.24; MS (FAB): m/z=540 (MH$^+$).

Intermediate 27

N-Isopropyl-N-(4-methoxy-phenyl)-2-phenylamino acetamide

A mixture of N-Isopropyl-N-(4-methoxy-phenyl) bromoacetamide (257.6 g 924 mmol), 1,2-phenylene diamine (100 g, 924 mmol) and potassium carbonate (128 g, 924 mmol) in DMF (1200 ml) was stirred at 0° for 2 h and then allowed to stir at rt for 20 h. The reaction mixture was filtered through celite and the filtrate concentrated in vacuo The resultant residue was dissolved in EtOAc (1200 ml), washed with water (3×200 ml), brine (200 ml), dried (MgSO4) and concentrated in vacuo. After removal of about 70% of the solvent a precipitate formed which was removed by filtration and washed with cold EtOAc and dried to afford the title compound (67.1 g) as a beige solid. The combined filtrates were concentrated in vacuo to afford a dark oil (88 g). Two Recrystallisations from ethanol afforded a second batch of the title compound as a beige solid (29.6 g).1H NMR (300 MHz, DMSO-d6). s 7.22 (m, 2H), 7.05(m, 2H), 6.47 (m, 1H), 6.34 (m, 2H), 5.95 (m, 1H), 4.81 (sept., 1H, J=6.8 ), 4.59 (dt, 1H, J=27.2, 6.1), 4.4 (s, 2H), 3.77 (s, 3H), 3.30 (s, 2H), 0.96 (d, 6H, J =6.8).

Intermediate 28

2-(2,4-dioxo-2,3,4,5-tetrahydrobenzo[b][1,4]diazepin-1-yl)-N-isopropyl-N-(4-methoxy-phenyl) acetamide A solution of N-Isopropyl-N-(4-methoxy-phenyl)-2-phenylamino acetamide.(20 g, 63.8 mmol) in THF (500 ml) and a solution of malonyl dichloride (6.2 ml, 63.8 mmol) in THF (500 ml) were added simultaneously over 40 min to THF (100 ml) and the resultant solution stirred at rt for 72 h after which time a further 3.0 ml of malonyl dichloride was added. 5 h later the solvents were removed in vacuo and the residue dissolved in methylene dichloride (300 ml) and washed with 2N aqueous sodium bicarbonate (2×200 ml). The combined organics were washed with water (2×200 ml), brine (200 ml), dried (MgSO4) and concentrated in vacuo to afford the crude product (23.8 g). This was then triturated extensively with ether and the resultant brown solid then purified by flash column chromatography eluting with 5% methanol in methylene chloride to afford the title compound (8.85 g) as a beige solid. 1H NMR (300 MHz, CDCl-3). s 7.7 (s, 1H), 7.4 (m, 1H), 6.90–7.3 (m, 7H), 4.97 (sept., 1H, J=6.8), 4.4 (m, 1H), 3.81 (s, 3H), 3.78 (m, 1H), 3.40 (s, 2H), 1.06 (d, 6H, J=6.8).

Intermediate 29

2-(2,4-dioxo-5-pyridin-3-yl-2,3,4,5-tetrahydrobenzo[b][1,4]diazepin-1-yl]-N-isopropyl-N-(4-methoxy-phenyl)acetamide A mixture of 2-(-2,4-dioxo-2,3,4,5-tetrahydrobenzo[b][1,4]diazepin-1-yl)-N-isopropyl-N-(4-methoxy-phenyl) acetamide (3.5 g 9.48 mmol), copper powder (1.09 g, 17.06 mmol) 3-bromopyridine (0.91 ml, 9.48 mmol) and potassium acetate (1.11 g, 11.37 mmol) in DMF (80 ml) was heated at 100° for 7 h. A further 0.4 ml of 3-bromopyridine was added and the resultant mixture stirred at 100° for a further 14 h. Copper powder (1.09 g, 17.06 mmol) 3-bromopyridine (0.91 ml, 9.48 mmol) and potassium acetate (1.11 g, 11.37 mmol) were added and the reaction mixture heated to 110° C. for 6 h. The solids were removed by filtration and the filtrate concentrated in vacuo and the residue was partitioned between ethyl acetate (150 ml) and 10% aqueous ammonium hydroxide solution (150 ml). The combined organics were washed with water (2×100 ml), brine (50 ml), dried (MgSO4) and concentrated in vacuo to afford the crude product. This was triturated extensively with ether to afford the title compound (2.56 g) as a cream solid. 1H NMR (300 MHz, CDCl-3). s 7.86 (d, 1H, J=8.1), 7.01–7.43 (m, 10H), 6.92 (d, 1H, J=8.3), 5.05 (sept, 1H, J=6.8), 4.22 (m, 2H), 3.88 (s, 3H), 3.58 (dd, 2H, J=32.2, 12.0), 1.06 (m, 6H).

Intermediate 30

2-(3-Azido-2,4-dioxo-5-pyridin-3-yl-2,3,4,5-tetrahydrobenzo[b][1,4]diazepin-1-yl) -N-isopropyl-N-(4-methoxy-phenyl)acetamide Potassium hexamethyl disilazide (0.5M in toluene, 4.59 ml, 2.29 mmol) was added dropwise over seven minutes to a −78° solution of 2-(2,4-dioxo-5-pyridin-3-yl-2,3,4,5-tetrahydrobenzo[b][1,4]diazepin-1-yl]-N-isopropyl-N-(4-methoxy-phenyl)acetamide (750 mg, 1.64 mmol) in THF (15 ml) and the resultant solution stirred at −78° for 17 min. 2,4,6-triisopropyl-benzenesulfonyl azide (632 mg, 2.05 mmol) was added and the reaction mixture stirred at −78° for 4 min prior to the addition of acetic acid (0.235 ml) and the reaction mixture allowed to attain rt. The solvents were removed in vacuo to afford the crude product. This was purified by flash column chromatography eluting with 5% methanol in methylene chloride to afford the title compound (530 mg) as a colorless foam. 1H NMR (300 MHz, CDCl-3). s 7.96 (d, 1H, J=8.0), 6.91–7.43 (m, 11H), 5.05 (sept, 1H, J=6.8), 4.42 (d, 1H, J=12.1), 4.38 (s, 1H), 4.22 (d, 1H, J=12.1), 3.88 (s, 3H), 1.06 (m, 6H).

Intermediate 31

2-(3-Amino-2,4-dioxo-5-pyridin-3-yl-1,2,3,4,5-tetrahydrobenzo[b][1,4]diazepin-1-yl) -N-isopropyl-N-(4-methoxy-phenyl)acetamide A mixture of 2-(3-Azido-2,4-dioxo-5-pyridin-3-yl-2,3,4,5-tetrahydrobenzo[b][1,4]diazepin-1-yl)-N-isopropyl-N-(4-methoxy-phenyl)acetamide (530 mg, 1.06 mmol) and 10% palladium on carbon (53 mg) was stirred in ethanol (50 ml) under an atmosphere of hydrogen for 9 h. A further batch of palladium on carbon was added (53 mg) and the resultant mixture stirred for a further 16 h. The solids were removed by filtration through celite and the filtrate concentrated in vacuo to afford the title compound (520 mg) which was used without further purification. 1H NMR (300 MHz, CDCl-3). s 8.52 (m, 2H), 7.92 (d, 1H, J=8.0), 6.91–7.43 (m, 11H), 5.05 (sept, 1H, J=6.8), 4.42–4.22 (m, 3H,), 3.88 (s, 3H), 1.06 (m, 6H).

Intermediate 32

2-(2,4-Dioxo-5-pyridin-4-yl-2,3,4,5-tetrahydro-benzo[b][1,4]diazepin-1-yl) -N-isopropyl-N-(4-methoxy-phenyl)-acetamide To a stirring solution of 400 mg (1.08 mmol) of 1-[isopropyl-(4-methoxy-phenyl)-amino]-1,5-dihydro-benzo[b][1,4]diazepine-2,4-dione in 20 mL of DMF was added 212 mg (2.16 mmol, 2.0 equiv) of potassium acetate, 206 mg (3.25 mmol, 3.0 equiv) copper dust, and 245 mg (2.62 mmol, 2 equiv) of 4-bromopyridine. The resulting solution was heated at 122° C. for 7 h. The reaction mixture was filtered hot through a pad of celite, the pad was washed with 10 mL of methanol and the filtrate concentrated in vacuo. The residue was diluted with EtOAc (100 mL) and washed with 5% aq ammonium hydroxide (5×25 mL). The organic layer was separated, dried (MgSO4) and the solvents removed in vacuo. Purification of the material by silica gel flash chromatography using EtOAc/Hexanes/NH4OH (80:20:1) as eluent followed by recrystalization from EtOH afforded 80 mg (16%) of the title compound: 1H NMR (Acetone-d6, 300 MHz) d 8.57 (d, 1H, J=4.6), 7.46 (m, 3H), 7.31 (m, 4H), 6.97 (m, 3H), 4.86 (sept, 1H), 4.48 (d, 1H, J=16.8 ), 4.21 (d, 1H, J=16.8), 3.86 (s, 3H), 3.67 (d, 1H, J=12.2), 3.22 (d, 1H, J=12.2), 1.02 (m, 6H); low resolution MS (FAB) m/z 459.2 (MH+).

Intermediate 33

2-(3-Amino-2,4-dioxo-5-pyridin-4-yl-2,3,4,5,5a,9a-hexahydrobenzo[b][1,4]diazepin-1-yl)-N-isopropyl-N-(4-methoxy-phenyl)-acetamide To a stirred solution of 80 mg (0.175 mmol) 2-(2,4-Dioxo-5-pyridin-4-yl-2,3,4,5-tetrahydro-benzo[b][1,4]diazepin-1-yl)-N-isopropyl-N-(4-methoxy-phenyl )-acetamide in 3 mL DMF was added 0.210 mL (0.209 mmol, 1.2 equiv) 1N Sodium bis(trimethylsilyl)amide in THF at 0° C. After stirring 0.5 h, 62 mg (0.262 mmol; 1.5 equiv) O-(diphenylphosphinyl)hydroxylamine (Harger, J. C. S. Perkin I, 3284–3288 (1981)) was added and the reaction mixture stirred 16 h at ambient temperature. The reaction mixture was filtered and the filtrate concentrated in vacuo. The crude product was purified by flash chromatography on 5 g silica gel eluted successively with EtOAc (100 mL), DCM/CH3OH (19:1, 100 mL). Appropriate fractions were combined and concentrated in vacuo to give the title compound as a clear glass: low resolution MS (FAB) m/z 474.2 (MH+); TLC Rf=0.31 (DCM/CH3OH, 19:1)).

Intermediate 34

2-Amino-N-isopropyl-N-(4-methoxy-phenyl)-acetamide

A solution of 2.86 g of 2-bromo-N-isopropyl-N-(4-methoxy-phenyl)-acetamide (10 mmol) in 100 mL methanol was saturated with ammonia at 0° and left for 3 days at ambient temperature in a sealed flask. Methanol and ammonia were removed in vacuo and the residue was dissolved in 100 mL of chloroform and washed with water (2×50 mL).

The organic layer was dried over anhydrous MgSO4, filtered, concentrated in vacuo and dried under high vacuum to afford 2.7 g of the title compound as an oil. 1H NMR (300 MHz, CDCl3) d 6.96 (m, 4H), 4.99 (m, 1H), 3.84 (s, 3H), 2.97 (s, 2H), 1.58 (s, 2H), 1.05 (d, 6H, J=6.6); low resolution MS (ESI)m/e 223 (MH+).

Intermediate 35

2-(4-Fluoro-2-nitro-phenylamino)-N-isopropyl-N-(4-methoxy-phenyl)-acetamide

A mixture of 9.06 g of 2,5-difluoro-nitrobenzene (60 mmol) and 12.64 g of 2-amino-N-isopropyl-N-(4-methoxy-phenyl)-acetamide (60 mmol, 1.0 equiv) were combined in 225 mL of 2:1 ethanol/water and heated to reflux under nitrogen and stirred vigorously overnight (approx. 16 hrs.). The resulting slurry was cooled to ambient temperature, filtered and washed with 2:1 water/ethanol. The wet solid was dissolved in methylene chloride, dried over anhydrous sodium sulfate, and evaporated in vacuo. The residue was triturated with hexane, filtered and washed with hexane. The product was dried under high vacuum to provide 9.32 g of the title compound as an orange solid. 1H NMR (300 MHz, CDCl3) d 7.89 (dd, 1H, J=3.1, 9.3), 7.12 (m, 3H), 6.99 (m, 2H), 6.35 (dd, 1H, J=4.8, 9.2), 5.03 (m, 1H), 3.89 (s, 3H), 3.57 (s, 2H), 1.09 (d, 6H, J=6.8); low resolution MS (ESI) m/e 362 (MH+).

Intermediate 36

2-(2-Amino-4-fluoro-phenylamino)-N-isopropyl-N-(4-methoxy-phenyl)-acetamide

A solution of 30 mL ethyl acetate, 175 mL ethanol, and 2.50 g of 2-(4-Fluoro-2-nitrophenylamino)-N-isopropyl-N-(4-methoxy-phenyl)-acetamide (6.92 mmol) was combined with 0.25 g of palladium on carbon (10 wt %) and hydrogenated under a hydrogen balloon over 16 hrs. The reaction mixture was filtered and evaporated in vacuo to provide 1.91 g of the title compound as a solid. 1H NMR (300 MHz, CDCl3) d 7.03 (m, 2H), 6.94 (m, 2H), 6.36 (m, 3H), 4.99 (m, 1H), 4.37 (b, 3H), 3.86 (s, 3H), 3.39 (s, 2H), 1.07 (d, 6H, J=6.8); low resolution MS (FAB)m/e 332 (MH+).

Intermediate 37

2-(7-Fluoro-2,4-dioxo-2,3,4,5-tetrahydro-benzo[b][1,4]diazepin-1-yl)-N-isopropyl-N-(4-methoxy-phenyl)-acetamide A solution of 1.724 g of 2-(2-amino-4-fluoro-phenylamino)-N-isopropyl-N-(4-methoxy-phenyl)-acetamide (5.20 mmol) in 15 mL of tetrahydrofuran was transferred to an addition funnel. A solution of 0.506 mL of malonyl dichloride (5.20 mmol, 1.0 equiv) in 15 mL tetrahydrofuran was transferred to a separate addition funnel. Each solution of each reagent was simultaneously added dropwise over 30 min. to 100 mL of tetrahydrofuran at ambient temperature under nitrogen with vigorous agitation. After stirring for 20 min. at ambient temperature, an additional 0.506 mL of malonyl dichloride (5.20 mmol, 0.1 equiv) was added in a single portion. The reaction was allowed to stir an additional 2.5 hrs. and then evaporated in vacuo to a residue. The residue was purified on flash grade silica gel with 1:3 ethyl acetate/hexane followed by 3:1 ethyl acetate/hexane. The appropriate fractions were combined, evaporated in vacuo to a residue and triturated with hexane. The hexane was removed in vacuo and the residual solid was dried under high vacuum to provide 1.061 g of the title compound as a tan solid. 1H NMR (300 MHz, CDCl3) d 8.14 (b, 1H), 7.45 (dd, 1H, J=5.5, 9.2), 7.29 (m, 1H), 7.05 (m, 1H), 6.94 (m, 3H), 6.78 (m, 1H), 4.99 (m, 1H), 4.37 (d, 1H, J=16.4), 3.82 (s, 3H), 3.69 (d, 1H, J=16.0), 3.40 (m, 2H), 1.09 (d, 6H, J=6.8); low resolution MS (FAB)m/e 400 (MH+).

Intermediate 38

2-(7-Fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide A mixture of 0.880 g of 2-(7-Fluoro-2,4-dioxo-2,3,4,5-tetrahydrobenzo[b][1,4]diazepin-1-yl)-N-isopropyl-N-(4-methoxy-phenyl)-acetamide (2.20 mmol), 420 mg of copper (bronze, 6.61 mmol, 3 equiv), 476 mg of potassium acetate (4.85 mmol, 2.2 equiv), and 0.290 mL of 3-bromopyridine (4.85 mmol, 2.2 equiv) in 10 mL of dimethylformamide was heated at 100° C. under nitrogen for 3 hrs. An additional 0.132 mL of 3-bromopyridine (2.43 mmol, 1.1 equiv) was added and the reaction was maintained for an additional 2 hrs. The reaction mixture was cooled to ambient temperature, filtered through a sintered glass funnel and then evaporated in vacuo to a residue. The residue was partitioned between ethyl acetate and aqueous ammonium hydroxide (5 mL conc. diluted to 100 mL). After separating the layers, the organic layer was washed with aqueous ammonium hydroxide (5 mL conc. diluted to 100 mL), and then saturated aqueous brine. The organic phase was then extracted three times with aqueous HCl (1N). The acid layers were combined and neutralized with aqueous sodium hydroxide (1N). The neutralized mixture was extracted twice with methylene chloride. The methylene chloride layers were combined, dried over anhydrous sodium sulfate, filtered and evaporated in vacuo to a residue. The residue was triturated with hexane and then concentrated in vacuo to provide 0.705 g of the title compound as a tan solid. H NMR (300 MHz, CDCl3) d 8.60 (m, 2H), 8.08 (b, 1H), 7.54 (b, 1H), 7.39 (m, 1H), 7.15 (m, 2H), 7.00 (m, 3H), 6.57 (dd, 1H, J=2.7, 9.2), 4.95 (m, 1H), 4.32 (d, 1H, J=17.9), 4.14 (d, 1H, J=17.8), 3.85 (s, 3H), 3.61 (d, 1H, J=12.1), 3.52 (d, 1H, J=12.1), 1.06 (d, 6H, J=6.8); low resolution MS (FAB)m/e 477 (MH+).

Intermediate 39

3-Nitro-benzoic acid t-butyl ester

Potassium t-butoxide solid (3.82 g, 32.30 mmol) was added to a solution of 3-nitrobenzoyl chloride (5.00 g, 26.94 mmol) in dry tetrahydrofuran (70 mL) and stirred under nitrogen for 2 hrs. The reaction mixture was concentrated in vacuo and partitioned between dichloromethane and water. After separating the phases, the aqueous layer was back-extracted with ethyl acetate. The organic layers were combined, dried over anhydrous magnesium sulfate, filtered and then concentrated in vacuo. The crude product was purified on flash grade silica gel using 0–5% gradient of ethyl acetate in n-hexane. Fractions containing the product were combined, concentrated in vacuo, and then dried under high vacuum to provide 3.82 g of the title compound as an oil. 1H NMR (300 MHz, CDCl3) d 8.79 (m, 1H), 8.35 (m, 2H), 7.62 (m, 1H), 1.63 (s, 9H); low resolution MS (CI) m/e 224 (MH+).

Intermediate 40

3-Amino-benzoic acid t-butyl ester

A solution of 3-nitro-benzoic acid t-butyl ester (3.77 g, 16.9 mmol) in absolute ethanol (50 mL) was combined with palladium on carbon (10 wt %, 0.30 g) and hydrogenated under a baloon of hydrogen gas for appoximately 3 hrs. The reaction mixture was filtered through a pad of diatomaceous earth and then concentrated in vacuo to an oil which crystallized when dried under high vacuum providing 3.28 g of the title compound as a tan solid. 1H NMR (300 MHz, CDCl3) d 7.38 (d, 1H, J=8.0 Hz), 7.29 (m, 1H), 7.19 (m, 1H), 6.83 (m, 1H), 1.58 (s, 9H); low resolution MS (CI) m/e 194 (MH+).

Intermediate 41

3-[(4-Nitrophenyl)oxycarbonyl]-amino-benzoic acid tert-butyl ester

A solution of 4-nitro-phenylchloroformate in dry dichloromethane (25 mL) was added dropwise over 20 min. to a solution of 3-amino-benzoic acid t-butyl ester (3.15 g, 16.24 mmol) and anhydrous pyridine (1.379 mL, 17.05 mmol) in anhydrous dichloromethane (25 mL) under nitrogen at 0–5_ C. The reaction mixture was allowed to warm to ambient temperature and stir overnight. After washing with aqueous HCl (1N), the reaction solution was dried over anhydrous magnesium sulfate and concentrated in vacuo to a solid. The crude product was slurried in n-hexane for 30 min., filtered and dried under high vacuum to provide 4.460 g of the title compound as a white crystalline solid. 1H NMR (300 MHz, CDCl3) d 8.30 (m, 2H), 7.92 (m, 1H), 7.78 (d, 2H, J=7.5 Hz), 7.43 (m, 3H), 7.11 (bs, 1H), 1.69 (s, 9H); low resolution MS (L-SIMS) m/e 358 (M+).

Intermediate 42

2-(3-Azido-7-Fluoro-2,4-dioxo-5-pyridin-3-yl-2,3,4,5-tetrahydrobenzo[b][1,4]diazepin-1-yl)-N-isopropyl-N-(4-methoxy-phenyl)-acetamide A solution of 262 mg of 2-(7-Fluoro-2,4-dioxo-5-pyridin-3-yl-2,3,4,5-tetrahydrobenzo[b][1,4]diazepin-1-yl)-N-isopropyl-N-(4-methoxy-phenyl)-acetamide (0.550 mmol) in 5 mL of anhydrous tetrahydrofuran at −78° C. under nitrogen was treated dropwise with 1.54 mL of potassium bis(trimethylsilyl)amide (0.5M in toluene, 0.770 mmol, 1.4 eq). After stirring 15 min., 212 mg of 2,4,6-triisopropylbenzenesulfonyl azide (0.687 mmol, 1.25 eq, J. Org. Chem. 1984, 49, 1430–1434) was added. After stirring 4 min., the reaction mixture was quenched by addition of 78.6 mL of glacial acetic acid (1.38 mmol, 2.5 eq) and allowed to warm to ambient temperature. The reaction mixture was evaportated in vacuo to a residue and purified on flash grade silica with 1:1 ethyl acetate / hexane. The appropriate fractions were combined, evaporated in vacuo and dried under high vacuum to provide 170 mg of the title compound as an amorphous solid. Low resolution MS (FAB)m/e 518 (MH+); TLC (silica) 3:1 Ethyl acetate: hexane Rf=0.68.

Intermediate 43

2-(3-Amino-7-Fluoro-2,4-dioxo-5-pyridin-3-yl-2,3,4,5-tetrahydrobenzo[b][1,4]diazepin-1-yl)-N-isopropyl-N-(4-methoxy-phenyl)-acetamide A solution of 152 mg of 2-(3-azido-7-fluoro-2,4-dioxo-5-pyridin-3-yl-2,3,4,5-tetrahydro-benzo[b][1,4]diazepin-1-yl)-N-isopropyl-N-(4-methoxy-phenyl)-acetamide in 10 mL of ethyl acetate was combined with 60 mg of palladium on carbon (10 wt %) and hydrogenated under a balloon of hydrogen gas for 16 hrs. The mixture was filtered, evaporated in vacuo and purified on flash grade silica gel using 3:7 methanol/ethyl acetate. The appropriate fractions were combined, evaporated in vacuo and dried under high vacuum to provide 82 mg of the title compound as a foam. Low resolution MS (FAB)m/e 492 (MH+); TLC (silica) 95:5 dichloromethane/methanol Rf=0.30.

Pharmacy Example

| Tablet | |
|---|---|
| Active Ingredient: | 50 mg |
| Lactose anhydrous USP: | 163 mg |
| Microcrystalline Cellulose NF: | 69 mg |
| Preglatinized starch Ph. Eur. | 15 mg |
| Magnesium stearate USP | 3 mg |
| Compression weight: | 300 mg |

The active ingredient, microcrystaline cellulose, lactose and preglelatinized starch are sieved through a 500 micron sieve and blended in a suitable mixer. The magnesium stearate is sieved through a 250 micron sieve and blended with the active blend. The blend is compressed into tablets using suitable punches, then coated with cellulose acetate phthalate.

CCK-A RECEPTOR BINDING ASSAY

Tissue Preparation:

Solutions of 0.3M sucrose and 2.0M sucrose were prepared and chilled overnight at 4° C. On the following day, inhibitors were added such that the final concentrations were 0.01% Soybean Trypsin Inhibitor (50 mg/500 ml sucrose) and 100 mM phenylmethysulfonyl fluoride (8.5 mg/500 mL sucrose).

Rats were sacrificed by decapitation using a guillotine. The rat's external abdominal wall was wetted with methanol and fur and skin were removed. The abdomen was opened, the pancreas was carefully dissected out and placed in a 50 mL beaker containing 0.3M sucrose. After all the pancreata were harvested, excess fat and lymph nodes were trimmed off. Pancreatic tissue was divided into approximately 4.0 g aliquots into 30 mL beakers, each containing 1.0 mL of 0.3M sucrose.

In 4° C. cold room, the pancreata were minced with scissors and diluted 1:10 weight:volume with 0.3M sucrose. Aliquots were homogenized in a chilled 40 mL Wheaton dounce with 4 up and down strokes of the "B" pestle followed by 4 up and down strokes of the "A" pestle. Homogenates were filtered through 2 layers of cheesecloth into a chilled 500 mL beaker, then diluted with 2.0M sucrose with stirring to yield a final concentration of 1.3M sucrose homogenate. The resulting 1.3M homogenate was dispensed into 18 thin-walled 36 mL polyallomer tubes on ice (approximately 30 mL homogenate per tube) and each tube was subsequently overlaid with 0.3M sucrose until liquid was approximately 0.5 cm from the top of the tube. The samples were spun in a Sorvall RC70 ultracentrifuge at 27,500 RPM (100,000×g) for 3 hours at 4° C. The interface band was collected into a chilled graduated cylinder, diluted and mixed with cold distilled water to a total volume of 312 mL and spun at 100,000×g for 50 min. at 4° C. The pellets were resuspended in KRH buffers, transferred to a 15 mL Wheaton dounce and homogenized with 4 up and down strokes of the matched "A" (tight) pestle. This homogenate was transferred into 2–27 mL polycarbonate bottles and spun at 100,000×g for 30 min. at 4° C. The pellet was resuspended (1 mL KRH buffer/gm wf. of original tissue), transferred to an appropriate size dounce and homogenized with 4 up and down strokes of the matched "A" pestle. 1 mL aliquots are stored at −70° C. in microcentrifuge tubes.

| KRH Buffer: pH = 7.4 at 4° C. | | |
|---|---|---|
| COMPONENT | MW | g/1 L |
| 25 mM HEPES | 260.3 | 6.51 |
| 104 mM NaCl | 58.44 | 6.08 |
| 5 mM KCl | 74.56 | 0.37 |
| 1 mM KPO$_4$ | 136.09 | 0.14 |
| 1.2 mM MgSO$_4$ | 246.48 | 0.30 |
| 2 mM CaCl$_2$ | 110.99 | 0.22 |
| 2.5 mM Glucose | 180.16 | 0.45 |
| 0.2% BSA | — | 2.00 |
| 0.1 mM PMSF* | 174.2 | 0.017 |
| 0.01% STI* | — | 0.10 |

*inhibitors added fresh the day of the experiment

Assay:

Test compounds were diluted in assay binding buffer in stock concentrations 10-fold more concentrated than desired final assay concentration.

50 mL compound+400 mL buffer+25 mL [$^{125}$I] sulphated CCK-8 labeled with Bolton and Hunter reagent (Amersham, 2000 Cl/mmol)+25 mL prepared rat pancreas membranes were incubated for 30 minutes at 25° C. while shaking gently throughout the incubation.

1 mM L-364718 (final concentration) was used for determination of non-specific binding.

Reaction was stopped using Brandell Cell Harvester, washing 3×with 3 mL ice-cold (4° C.) assay binding buffer per wash.

Tissues were collected on Whatman GF/B filter papers pre-wet with assay buffer and filter papers counted using a gamma counter.

CCK-B RECEPTOR BINDING ASSAY

Tissue Preparation:

Hartley Male Guinea Pigs (250–300 g, Charles River) were sacrificed by decapitation. The brain was removed and placed in 4° C. buffer (buffer=50 mM Tris/HCL, pH =7.4). The cortex was dissected and placed in 40° C. buffer. The total wet weight of all cortices was determined and the tissues were diluted 1:10 (wt:vol) with buffer.

The cortex was minced using a Tekmar Tissuemizer then homogenized in buffer with 5 up and down strokes using a motor driven glass/teflon homogenizer. The preparation was maintained at 4° C. (on ice).

Membranes were pelleted by centrifugation in Sorvall RC5C at 4° C. using a SA 600 rotor spun at 16,000 RPM (47,800×g Maximum). The pellet was saved and the supernatent was discarded. The pellets were combined and resuspended in buffer at 4° C. using same volume as above and blended as above with 5 up and down strokes of a glass/teflon motor driven homogenizer using the same volume as before. The resulting homogenates were spun at 16,000 RPM (47,800×g Maximum, 36,592×g Average) for 15 minutes at 4° C. Pellets were saved and the supernatents discarded. Pellets were subsequently combined with buffer to get a final volume of 300 mL and blended using a Tekmar Tissuemizer. Initial protein content was determined by the Biorad protein assay. The volume of suspension was adjusted with buffer, such that the volume adjustment yielded approximately 4.0 mg/mL as a final concentration, confirmed via the Biorad protein assay. The final suspension was transferred as 4.0 mL aliquots into plastic tubes and frozen at −70° C.

Assay:

Buffer=20 mM HEPES, 1 mM EGTA, 118 mM NaCl, 5 mM KCL, 5 mM MgCl$_2$, 0.05% BSA at pH=7.4.

Skatron filters were soaked in buffer with 0.1% Bovine Serum Albumin (BSA) for an hour prior to harvesting.

100 mM Bestatin and 3 mM Phosphoramidon were prepared fresh. (Final assay concentrations will=10 mM respectfully.)

Test compounds were diluted in assay binding buffer in stock concentrations 10-fold more concentrated than desired final assay concentrations. [$^{125}$I]-sulfated CCK-8 labeled with Bolton-Hunter reagent (Amersham, 200 Ci/mmol) was diluted.

25 mL 100 mM Bestatin+25 mL 3 mM Phosphoramidon+ 25 mL test compound+50 mL radioligand+25 mL buffer+ 100 mL guinea pig cortex membranes were incubated 150 minutes at room temperature.

For B$_0$ determination, assay binding buffer was substituted for test compound.

For filter binding determination, assay buffer was substituted for test compound and guinea pig cortex membranes.

For non-specific binding determination, 1 mM sulphated CCK-8 (Sigma) was substituted for test compound.

Reaction was stopped by filtering using the automated Skatron Cell Harvester. The filters were rinsed using 4° C. buffer. The filters were subsequently punched, placed in tubes and counted using a gamma counter.

GUINEA PIG GALL BLADDER ASSAY

Tissue Preparation:

Gallbladders were removed from guinea pigs sacrificed by cervical dislocation. The isolated gallbladders were cleaned of adherent connective tissue and cut into two rings from each animal (2–4 mm in length). The rings were subsequently suspended in organ chambers containing a physiological salt solution of the following composition (mM): NaCl (118.4); KCl (4.7); MgSO$_4$×H$_2$O (1.2); CaCl$_2$× 2H$_2$O (2.5); KH$_2$PO$_3$ (1.2); NaHCO$_3$ (25) and dextrose (11.1). The bathing solution was maintained at 37° C. and aerated with 95% O$_2$/5%CO$_2$. Tissues were connected via gold chains and stainless steel mounting wires to isometric force displacement transducers (Grass, Model FT03 D). Responses were then recorded on a polygraph (Grass, Model 7E). One tissue from each animal served as a time/solvent control and did not receive test compound.

Assay:

Rings were gradually stretched (over a 120 min. period) to a basal resting tension of 1 gm which was maintained throughout the experiment. During the basal tension adjustment period, the rings were exposed to acetylcholine (ACH, 10$^{-6}$M) four times to verify tissue contractility. The tissues were then exposed to a submaximal dose of sulfated CCK-8 (Sigma, 3×10$^{-9}$M). After obtaining a stable response, the tissues were washed out 3 times rapidly and every 5 to 10 minutes for 1 hour to reestablish a stable baseline.

Compounds were dissolved in dimethylsulfoxide (DMSO) then diluted with water and assayed via a cumulative concentration-response curve to test compound (10$^{-11}$ to 3×10$^{-6}$M) followed by a concentration-response curve to sulfated CCK-8 (10$^{-10}$ to 10$^{-6}$M) in the presence of the highest dose of the test compound. As a final test, ACH (10 mM) was added to induce maximal contraction. A minimum of three determinations of activity were made for each test compound.

Results obtained in this test with representative compounds of the invention are given below. The compounds were tested at a concentration of 1 μM and the results expressed as % sulfated CCK-8 maximal response.

| Example No. | Contraction |
|---|---|
| 1 | 91 |
| 2 | 64 |
| 3 | 83 |
| 4 | 67 |
| 5 | 51 |
| 6 | 32 |
| 7 | 77 |
| 8 | 81 |
| 10 | 83 |
| 11 | 67 |
| 13 | 96 |
| 14 | 84 |
| 15 | 93 |

18-HOUR DEPRIVATION-INDUCED FEEDING PARADIGM

Male, Long-Evans rats (Charles River Co., Raleigh, N.C.), weighing 300–375 grams, were acclimated individually for at least a week in hanging, stainless steel mesh cages (17.8×25.4×17.8 cm high) with ad libitum access to water (delivered through automatic drinking spouts at the rear of the cage) and food (Lab Blox, Purina Rodent Laboratory Chow #5001) on a 12-hour light/dark cycle (lights on from 0600–1800 hours, or h) at approximately 22.8° C. Prior to testing, all chow, but not water, was removed at 1600 h. At 0900 h the next morning, rats were weighed. At 0945 h, rats were injected intraperitoneally (i.p.), orally (per os, or p.o.) or through an indwelling, intra-duodenal cannulea with a test compound or vehicle (2 mL/kg) and returned to their home cages. Food was presented at 1000 h. At 1030 h, remaining food and spillage was weighed.

Compounds of the invention are essentially non toxic at therapeutically useful doses. Thus no untoward effects were observed when the compounds were administered to rats at therapeutically useful dose levels.

We claim:
1. A compound of the formula (I)

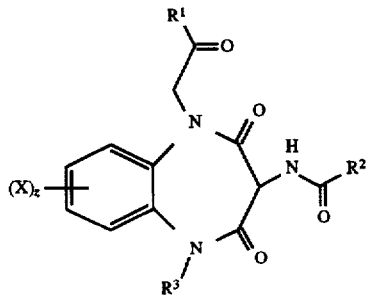

and physiologically salts thereof wherein

X is either hydrogen, trifluoromethyl, alkyl, $C_{1-4}$alkylthio, —O($C_{1-4}$alkyl) or halogen;

$R^1$ is either Formula II or —$NR^4R^5$.;

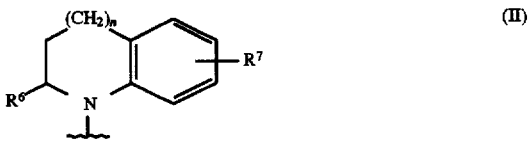

$R^2$ is either:
(1) a heterocycle linked at its 2-position and selected from pyrrole, tetrahydropyrrole, indole, benzofuran, thiophene, benzothiophene, indoline, quinoline or 4-oxobenzopyran and wherein said pyrrole, tetrahydropyrrole, indole or indoline may optionally be substituted on the ring nitrogen thereof by the group $R^8$ as defined hereunder and said indole, indoline, quinoline, benzofuran, benzothiophene or 4-oxobenzopyran may optionally be substituted in the benzo ring thereof by the group $R^9$ as defined hereunder or (2) phenyl or phenyl mono- or disubstituted independently with halogen, hydroxy, cyano, carboxy, —O($C_{1-4}$alkyl), —O($CH_2C_6H_5$), —COO($C_{1-4}$alkyl), amino, dimethylamino, —$NHR^{16}$, 1-pyrrolidinyl or tetrazolyl; or (3) pyridine or pyridinyl mono- or disubstituted independently with halogen, methyl, hydroxy, nitro, cyano, carboxy, —O($C_{1-4}$alkyl), —O($CH_2C_6H_5$), —COO($C_{1-4}$alkyl), amino or dimethylamino; or (4) —$NHR^{11}$ where $R^{11}$ is defined hereinunder or $R^{11}$ is 7-indazolyl containing a group $R^{10}$ at the N–1 position;

$R^3$ is a heterocyclic group (attached to the rest of the molecule via a carbon atom ring member thereof), selected from pyridyl, pyrimidinyl, pyridazinyl, pyrazinyl, furanyl, thiophenyl, pyrrolyl, oxazolyl, thiazolyl, imidazolyl, pyrazolyl, isoxazolyl, isothiazolyl, oxadiazolyl, thiazolyl, thiadiazole, pyrrolidinyl, piperidinyl, morpholinyl or thiomorpholinyl which heterocyclic groups may be substiuted with up to 3 substituents which may be the same or different and selected from halogen, $C_{1-4}$alkyl, nitro, carboxyl, $C_{1-4}$alkoxycarbonyl, $C_{1-4}$alkoxy, $C_{1-4}$alkylthio, amino, $C_{1-4}$alkylamino or di($C_{1-4}$alkyl)amino;

$R^4$ is independently $C_{3-6}$alkyl, $C_{3-6}$cycloalkyl, $C_{3-6}$alkenyl, phenyl, —$(CH_2)_pCN$ or —$(CH_2)_pCOO$($C_{1-4}$alkyl) and $R^5$ is independently $C_{3-6}$alkyl, $C_{3-6}$cycloalkyl, $C_{3-6}$alkenyl, benzyl, phenyl or phenyl mono- or disubstituted independently with $C_{1-3}$alkyl optionally substituted by one or more fluorine atoms, cyano, hydroxy, dimethylamino, —O($C_{1-4}$alkyl), —O($CH_2C_6H_5$), —NH($C_{1-4}$alkyl), —COO($C_{1-4}$alkyl), —N($C_{1-4}$alkyl)$_2$ pyrrolidino, morpholino or halogen or $R^4$ is $C_{1-2}$alkyl and $R^5$ is phenyl substituted at the 2- or 4- position with chloro, methyl, methoxy or methoxycarbonyl;

$R^6$ is hydrogen or methyl;

$R^7$ is hydrogen, hydroxy, fluoro, dimethylamino, —O($C_{1-4}$alkyl) or —O($CH_2C_6H_5$);

$R^8$ is —$(CH_2)_kCOOH$;

$R^9$ is methyl, chloro, nitro, hydroxy, methoxy or —$NHR^{10}$;

$R^{10}$ is hydrogen, acetyl, $C_{1-4}$alkyl, —$SO_3H$, —$SO_2CH_3$, —$SO_2CF_3$ or —$SO_2C_6H_5$, $C_{1-4}$alkoxycarbonyl;

$R^{11}$ is phenyl or phenyl mono- or disubstituted independently with fluorine, trifluoromethoxy, $C_{1-4}$alkylthio, —(CH$_2$)$_c$COOH, —(CH$_2$)$_c$COO(C$_{1-4}$alkyl), —(CH$_2$)$_c$SCH$_3$, —(CH$_2$)$_c$SOCH$_3$, —(CH$_2$)$_c$SO$_2$CH$_3$, —(CH$_2$)$_c$CONH$_2$, —SCH$_2$COOH, —CONH(SO$_2$CH$_3$), —CONH(SO$_2$CF$_3$), —(CH$_2$)$_c$N(C$_{1-4}$alkyl)$_2$, —(CH$_2$)$_c$(SO$_2$CF$_3$), —(CH$_2$)$_c$N(SO$_2$CF$_3$)(C$_{1-4}$alkyl), —(CH$_2$)$_c$SO$_2$NHCO(C$_{1-4}$alkyl), —(CH$_2$)$_c$SO$_2$N(C$_{1-4}$alkyl)CO(C$_{1-4}$alkyl), —(CH$_2$)$_c$CONHSO$_2$(C$_{1-4}$alkyl), —(CH$_2$)$_c$CON(C$_{1-4}$alkyl)SO$_2$(C$_{1-4}$alkyl), —(CH$_2$)$_c$OR$^{12}$— (CH$_2$)$_c$NHR$^{10}$ or phenyl monosubstituted with —(CH$_2$)$_c$(tetrazolyl), —(CH$_2$)$_c$(carboxamidotetrazolyl) or —(CH$_2$)$_c$(pyrrolidinyl) or R$^{11}$ is selected from pyridine or pyridinyl mono- or disubstituted independently with halogen, methyl, hydroxy, nitro, cyano, carboxy, —O(C$_{1-4}$ alkyl), amino, dimethylamino, —NHR$^{10}$;

R$^{12}$ is hydrogen, C$_{1-6}$alkyl, C$_{3-6}$cycloalkyl, —CH$_2$C$_6$H$_5$, —CH$_2$COOH, —CH$_2$CONH$_2$, —CH$_2$CONH(C$_{1-4}$alkyl), —CH$_2$CON(C$_{1-4alkyl})_2$ or

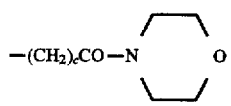

or

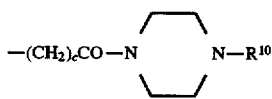

z is 1 or 2;
n is 1 or 2;
p is an integer from 1–4;
b is an integer from 0–3; and
c is 0 or 1.

2. A compound as claimed in claim 1 wherein R$^3$ is a pyridyl, pyrimidinyl or 1, 3, 5-trimethyl-1-H-pyrazol-4-yl group.

3. A compound as claimed in claim 1 wherein R$^3$ is a -3-pyridyl group.

4. A compound as claimed in claim 1 wherein R$^4$ is propyl or isopropyl and R$^5$ is phenyl optionally substituted in the para position by a group selected from hydroxy, methoxy, fluoro, dimethylamino, pyrrolidino or morpholino.

5. A compound as claimed in claim 1 wherein R$^4$ is isopropyl and R$^5$ is 4-methoxyphenyl.

6. A compound a claimed in claim 1 wherein R$^2$ is indole, optionally substituted phenyl or NHR$^{11}$.

7. A compound as claimed in claim 1 wherein R$^2$ is indole or NHR$^{11}$ wherein R$^{11}$ is phenyl or 3-carboxyphenyl.

8. A compound as claimed in claim 1 wherein X is hydrogen or fluorine.

9. H-indole-2-carboxylic acid {1[isopropyl-(4-methoxyphenyl)-carbamoylmethyl]-2,4-dioxo-5-pyridin-3-yl-2,3,4,5-tetrahydro-1H-benzo[b][1,4]diazepin-3-yl}-amide and enantiomers thereof.

10. A compound as claimed in claim 1 for use in therapy.

11. The use of a compound according to claim 1 in the manufacture of a medicament for the treatment of conditions where a modulation of the affects gastrin or CCK is of therapeutic benefit.

12. A method of treatment of a mammal including man for conditions where modulation of the effects of gastrin and/or CCK is of a therapeutic benefit comprising administration of an effective amount of a compound according to claim 1.

13. A pharmaceutical composition comprising a compound according to claim 1 in an admixture with one or more physiologically acceptable carriers or excipients.

14. A process for the preparation of a compound as defined in claim 1 which comprises:

reacting a compound of Formula (III) wherein R$^1$, R$^3$, R$^{11}$, X and z are as defined in Formula (I)

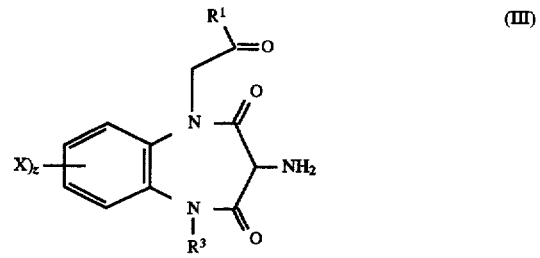

with a compound of Formula (IV)

wherein Y is the group —NCO, HNCOCl or NHCOR$_a$ where R$_a$ is a nitro substituted phenoxy group or a 1-imidazole group.

15. A process for the preparation of a compound as defined in claim 1, comprising the step of reacting a compound of Formula (V)

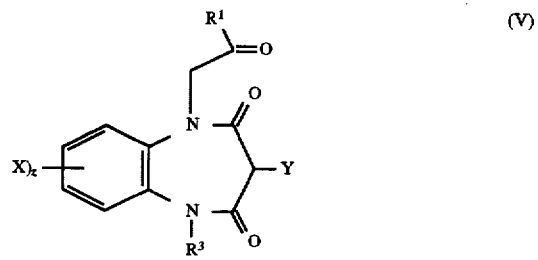

wherein R$^1$, R$^3$, X, and z have the meaning defined in Formula (I) and wherein Y is the group —NCO, —NHCOCl or NHCOR$_a$ wherein R$_a$ is a nitro substituted phenoxy group or a 1-imidazole group; with an amine of Formula (VI)

wherein R$^{11}$ has the meaning defined in Formula (I).

16. A process for the preparation of a compound as defined in claim 1, comprising the step of reacting a compound of Formula (VII) wherein R$^3$, R$^{11}$, and X are as defined in Formula (I)

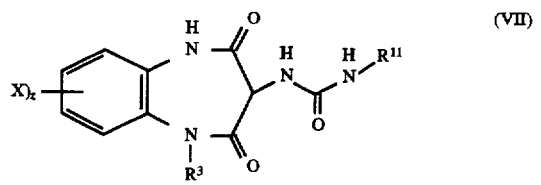

with a compound of Formula (VIII)

wherein R$^1$ has the meaning as defined in Formula (I) and hal is Cl or Br.

17. A process for the preparation of a compound as defined in claim 1, comprising the step of reacting a compound of Formula (III) wherein R$^1$, R$^3$, X, and Z are as defined in Formula (I)

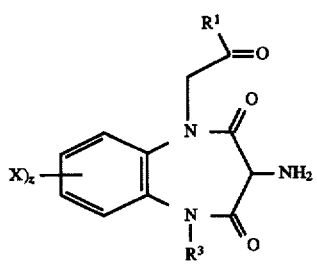 (III)
with an acid of Formula (IX)
$$HOOC-R^2 \quad (IX)$$
wherein $R^2$ has the meaning as defined in Formula (I).
* * * * *